US010684287B1

(12) United States Patent
Tang et al.

(10) Patent No.: US 10,684,287 B1
(45) Date of Patent: Jun. 16, 2020

(54) METHODS RELATED TO A STRUCTURE OF HIGH-AFFINITY HUMAN PD-1/PD-L2 COMPLEX

(71) Applicants: Chan Zuckerberg Biohub, Inc., San Francisco, CA (US); The Board of Trustees of the Leland Stanford Junior University, Stanford, CA (US)

(72) Inventors: Shaogeng Tang, Stanford, CA (US); Peter S. Kim, Stanford, CA (US)

(73) Assignees: Chan Zuckerberg Biohub, Inc., San Francisco, CA (US); The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/786,409

(22) Filed: Feb. 10, 2020

Related U.S. Application Data

(60) Provisional application No. 62/904,515, filed on Sep. 23, 2019, provisional application No. 62/907,335, filed on Sep. 27, 2019.

(51) Int. Cl.
*G01N 33/68* (2006.01)
*G16C 20/30* (2019.01)
*G16C 20/64* (2019.01)

(52) U.S. Cl.
CPC .......... *G01N 33/68* (2013.01); *G16C 20/30* (2019.02); *G16C 20/64* (2019.02); *G01N 2333/70521* (2013.01)

(58) Field of Classification Search
None
See application file for complete search history.

(56) References Cited

PUBLICATIONS

Abagyan et al., "High-throughput docking for lead generation", Current Opinion in Chemical Biology, Aug. 1, 2001, pp. 375-382, vol. 5, Issue 4, Elsevier, Amsterdam, Netherlands.
Abagyan et al., "Biased probability Monte Carlo conformational searches and electrostatic calculations for peptides and proteins", J. Comp. Chem., Jan. 20, 1994, pp. 983-1002, vol. 235, Issue 3, Academic Press, Cambridge, MA.
Adams et al., "PHENIX: a comprehensive Python-based system for macromolecular structure solution", Acta Crystallogr., Sect. D: Biol. Crystallogr., Feb. 2010, pp. 213-221, vol. 66, Part 2, International Union of Crystallography, Chester, England.
Arkin et al., "Small-molecule inhibitors of protein-protein interactions: progressing toward the reality", Chem. Biol., Sep. 18, 2014, pp. 1102-1114, vol. 21, Issue 9, Nature Reviews, United Kingdom.
Bash et al., "Free Energy Calculation by Computer Simulation", Science, May 1, 1987, pp. 564-568, vol. 236, Issue 4801, American Association for the Advancement of Science, Washington, D.C.
Bissantz et al., "Protein-based virtual screening of chemical databases. 1. Evaluation of different docking/scoring combinations", J Med Chem, Nov. 22, 2000, pp. 4759-4767, vol. 43, American Chemical Society, Washington, D.C.
Bloom, "An experimentally determined evolutionary model dramatically improves phylogenetic fit", Mol. Biol. Evol., May 24, 2014, pp. 1956-1978, vol. 31, Issue 8, Oxford University Press, Oxford, United Kingdom.
Boder, "Yeast surface display for screening combinatorial polypeptide libraries", Nat. Biotechnol., Jun. 1, 1997, pp. 553-557, 15, Springer Nature, London , Germany.
Borghaei et al., "Nivolumab versus Docetaxel in Advanced Nonsquamous Non-Small-Cell Lung Cancer", N Engl J Med., Oct. 22, 2015, pp. 1627-1639, 373, Massachusetts Medical Society, Waltham, MA.
Bowes et al., "Reducing safety-related drug attrition: The use of in vitro pharmacological profiling", Nature Review Drug Discovery, Dec. 2012, pp. 909-922 (11), Macmillan Publishers Limited, New York, NY.
Byun et al., "Cancer immunotherapy—immune checkpoint blockade and associated endocrinopathies", Nat Rev Endocrinol., 2017, Springer Nature, London , Germany.
Caulfield et al., "Small molecule mimetics of an HIV-1 gp41 fusion intermediate as vaccine leads", The Journal of Biological Chemistry, Oct. 13, 2010, pp. 40604-40611, 285, Journal of Biological Chemistry, Rockville, Maryland.
Chao et al., "Isolating and engineering human antibodies using yeast surface display", Nat Protoc., Jul. 13, 2006, pp. 755-768, vol. 1, No. 2, Springer Nature, London , Germany.
Cheng et al., "Structure and interactions of the human programmed cell death 1 receptor", The Journal of Biological Chemistry, Feb. 15, 2013, pp. 11771-11785, 288, Journal of Biological Chemistry, Rockville, Maryland.
Claussen et al., "FlexE: Efficient Molecular Docking Considering Protein Structure Variations", J. Molecular Biology, Apr. 27, 2001, pp. 377-395, vol. 308, Issue 2, Academic Press, Cambridge, MA.
Corbi-Verge et al., "Motif mediated protein-protein interactions as drug targets", Cell Commun Signal, Mar. 2, 2016, (14) 8, BioMed Central Ltd., London, United Kingdom.
Cornell, et al., "A second-generation force field for the simulation of proteins, nucleic acids, and organic molecules", J. American Chemical Society, Mar. 6, 1996, pp. 5179-5197, 117, ACS Publications, Washington, D.C.
Daniels et al., "Conformational Kinetics Reveals Affinities of Protein Conformational States", Proceedings of the National Academy of Sciences of the United States of America, Jul. 28, 2015, pp. 9352-9357, 112 (30), National Academy of Sciences, Washington, D.C.

(Continued)

*Primary Examiner* — Michael L Borin
(74) *Attorney, Agent, or Firm* — Kilpatrick Townsend & Stockton LLP; Elena S. Polovnikova

(57) ABSTRACT

Variants of human PD-1 comprising one or more of amino acid substitutions in residues corresponding to N74, T76 and A132 of SEQ ID NO:1 are described. Also described are structures, obtained using X-ray crystallography, of the human PD-1/PD-L2 complex and mutant PD-1 variants. The structures of human PD-1 described in the present disclosure are useful in drug discovery, including small-molecule drug discovery. Accordingly, methods of using the structures in drug discovery are also described.

29 Claims, 6 Drawing Sheets

Specification includes a Sequence Listing.

(56) References Cited

PUBLICATIONS

Ewing et al., "Critical Evaluation of Search Algorithms for Automated Molecular Docking and Database Screening", J. Computational Chemistry, Dec. 7, 1998, pp. 1175-1189, vol. 18 No. 9, Wiley, Hoboken, NJ.

Eyrisch et al., "Transient pockets on protein surfaces involved in protein-protein interaction", J. Med. Chem., Jun. 30, 2007, pp. 3457-3464, 50, ACS Publications, Washington, D.C.

Fowler et al., "Deep mutational scanning: a new style of protein science", Nat. Methods, Jul. 30, 2014 pp. 801-807, 11, Springer Nature, London , Germany.

Ganesan et al., "Comprehensive in vitro characterization of PD-L1 small molecule inhibitors", Sci Rep., Aug. 27, 2019, pp. 1-9, Springer Nature, London , Germany.

Gohlke et al., "Knowledge-based Scoring Function to Predict Protein-Ligand Interactions", J. Mol. Biol., Jan. 14, 2000, pp. 337-356, vol. 295, Issue 2, Elsevier, Amsterdam, Netherlands.

Guzik et al., "Small-Molecule Inhibitors of the Programmed Cell Death-1/Programmed Death-Ligand 1 (PD-1/PD-L1) Interaction via Transiently Induced Protein States and Dimerization of PD-L1", J. Med. Chem., Jun. 14, 2017, pp. 5857-5867, (60)13, ACS Publications, Washington, D.C.

Halgren et al., "Glide: a new approach for rapid, accurate docking and scoring. 2. Enrichment factors in database screening", J Med Chem., Feb. 27, 2004, pp. 1750-1759, vol. 47 No. 7, ACS Publications, Washington, D.C.

Head et al., "Validate: A New Method for Receptor-Based Prediction of Binding Affinities of Novel Ligand", J. American Chemical Society, Apr. 24, 1996, pp. 3959-3969, vol. 118, ACS Publications, Washington, D.C.

Holst et al., "Adaptive Multilevel Finite Element Solution of the Poisson~Boltzmann Equations I. Algorithms and Examples", J. Comp. Chem., Oct. 3, 2000, pp. 1319-1342, vol. 21, No. 15, Wiley, Hoboken, NJ.

Horita et al., "High-resolution crystal structure of the therapeutic antibody pembrolizumab bound to the human PD-1", Sci Rep., Oct. 13, 2016, pp. 1-8, Springer Nature, London , Germany.

Jackson et al., "Rapid Refinement of Protein Interfaces Incorporating Solvation: Application to the Docking Problem", J. Mol. Biol., Feb. 13, 1998, pp. 265-285, vol. 276, Issue 1, Elsevier, Amsterdam, Netherlands.

Jang, "Pharmacokinetics and its role in small molecule drug discovery research", Med Res Rev., Sep. 2001, pp. 382-396, vol. 21, Issue 5, Wiley, Hoboken, NJ.

Jiao et al., "Small molecules as PD-1/PD-L1 pathway modulators for cancer immunotherapy", Curr. Pharm. Des., 2018, pp. 4911-4920, vol. 24, No. 41, Ingenta, Oxford, United Kingdom.

Jones of al., "Development and Validation of a Genetic Algorithm for Flexible Docking", J. Mol. Biol., Apr. 4, 1997, pp. 727-748, vol. 267, Issue 3, Elsevier, Amsterdam, Netherlands.

Jones et al., "Molecular Recognition of Receptor Sites using a Genetic Algorithm with a Description of Desolvation", J. Mol. Biol., 1995, pp. 43-53, vol. 245, Issue 1, Elsevier, Amsterdam, Netherlands.

Jutz et al., "A cellular platform for the evaluation of immune checkpoint molecules", Oncotarget, Sep. 12, 2017, pp. 64892-64906, 8(39), Impact Journals, LLC, Orchard Park, NY.

Keiser, "In Silico Prediction of Drug Side Effects", in Antitargets and Drug Safety (eds L. Urbán, V. F. Patel and R. J. Vaz), Apr. 22, 2015 Chapter 2, pp. 19-44, Wiley-VCH Verlag GmbH & Co. KGaA, Weinheim, Germany.

Keizer, "Clinical pharmacokinetics of therapeutic monoclonal antibodies". Clin Pharmacokinet, 2010, pp. 493-507, 49, Springer Nature, London , Germany.

Kramer et al., "Evaluation of the FlexX incremental construction algorithm for protein-ligand docking", Proteins, Nov. 1, 1999, pp. 228-241, vol. 37, Issue 2, Wiley, Hoboken, NJ.

Labute et al., "Adverse Drug Reaction Prediction Using Scores Produced by Large-Scale Drug-Protein Target Docking on High-Performance Computing Machines", PloS One, Sep. 5, 2014, pp. 1-13, 9(9): e106298, PLOS, San Francisco, CA.

Lazar-Molnar et al., "Crystal structure of the complex between programmed death-1 (PD-1) and its ligand PD-L2", PNAS, May 7, 2008, pp. 10483-10488, 105(30), National Academy of Sciences, Washington, D.C.

Lazar-Molnar et al., "Structure-guided development of a high-affinity human Programmed Cell Death-1: Implications for tumor immunotherapy", EbioMedicine, Mar. 2017, pp. 30-44, vol. 17, Elsevier, Amsterdam, Netherlands.

Le et al., "Mismatch repair deficiency predicts response of solid tumors to PD-1 blockade", Science, Jul. 28, 2017, pp. 409-413, vol. 357, Issue 6349 AAAS, Washington, D.C.

Lee et al., "Structural basis of checkpoint blockade by monoclonal antibodies in cancer immunotherapy", Nat Commun., Oct. 31, 2016, pp. 1-10, Springer Nature, London , Germany.

Li et al., "High-affinity PD-1 molecules deliver improved interaction with PD-L1 and PD-L2", Cancer Sci. Aug. 2018, pp. 2435-2445, vol. 109, Issue 8, Wiley, Hoboken, NJ.

Lin et al., "The PD-1/PD-L1 complex resembles the antigen-binding Fv domains of antibodies and T cell receptors", PNAS, Feb. 26, 2008, pp. 3011-3016, 105 (8), National Academy of Sciences, Washington, D.C.

Liu, "The history of monoclonal antibody development—Progress, remaining challenges and future innovations", Ann Med Surg Dec. 2014, pp. 113-116, vol. 3, Issue 4, Elsevier, Amsterdam, Netherlands.

Lyu et al., "Ultra-large library docking for discovering new chemotypes", Nature, Feb. 6, 2019, pp. 224-229, 566, Springer Nature, London , Germany.

Marcus et al., "FDA Approval Summary: Pembrolizumab for the Treatment of Microsatellite Instability-High Solid Tumors", Clin. Cancer. Res., Jul. 2019, pp. 3753-3758, vol. 25, Issue 13, American Philadelphia, PA.

Maute et al., "Engineering high-affinity PD-1 variants for optimized immunotherapy and immuno-PET imaging", PNAS, Nov. 24, 2015, pp. E6506-E6514, 112 (47), National Academy of Sciences, Washington, D.C.

Mehler et al., "Electrostatic effects in proteins: comparison of dielectric and charge models", Protein Engineering, Dec. 1, 1991, pp. 903-910, vol. 4, Issue 8, Oxford University Press, Oxford, United Kingdom.

Mikitsh et al., "Pathways for small molecule delivery to the central nervous system across the blood-brain barrier", Perspect Medicin Chem., Jun. 16, 2014, pp. 11-24(6), SAGE Publications Ltd., Thousand Oaks, CA.

Minchinton et al., "Drug penetration in solid tumours", Nat. Rev. Cancer, 2006, pp. 583-592(6), Springer Nature, London , Germany.

Minor et al., "HKL-3000: the integration of data reduction and structure solution—from diffraction images to an initial model in minutes", Acta crystallographica, Section D, Biological crystallography, 2006, pp. 859-866, 62, International Union of Crystallography, Chester, United Kingdom.

Moal et al., "Kinetic rate constant prediction supports the conformational selection mechanism of protein binding", PLoS Comput Biol., p. 1-13, e1002351, vol. 8, Issue 1, PLOS, San Francisco, CA.

Modell et al., "Systematic Targeting of Protein-Protein Interactions", Trends Pharmacol. Sci., Aug. 2016, pp. 702-713, vol. 37, Issue 8, Elsevier, Amsterdam, Netherlands.

Morris et al., "Automated Docking Using a Lamarckian Genetic Algorithm and an Empirical Binding Free Energy Function", J. Comp. Chem., Nov. 1998, pp. 1639-1662, vol. 19, Issue 14, Wiley, Hoboken, NJ.

Na et al., "Structural basis for blocking PD-1-mediated immune suppression by therapeutic antibody pembrolizumab", Cell Res. Jun. 21, 2016, pp. 147-150, 27, Springer Nature, London , Germany.

Neuwelt et al., "Engaging neuroscience to advance translational research in brain barrier biology", Nat. Rev. Neurosci., Feb. 18, 2011, pp. 169-182, 12, Springer Nature, London , Germany.

(56) References Cited

PUBLICATIONS

Palade, "Studies on the endoplasmic reticulum, II. Simple dispositions in cells in situ", J Biophys Biochem Cytol, Nov. 25, 1955, pp. 567-582, vol. 1, Rockefeller University Press, New York, NY.

Pascolutti et al., "Structure and Dynamics of PD-L1 and an Ultra-High-Affinity PD-1 Receptor Mutant", Structure, Oct. 4, 2016, pp. 1719-1728, vol. 24, Issue 10, Cell Press.

Pearlman et al. "AMBER 4.1", University of California, San Francisco, pp. 1-41, (1995), Elsevier, Amsterdam, Netherlands.

Rarey et al. "A Fast Flexible Docking Method Using an Incremental Construction Algorithm", J. Mol. Biol., Aug. 23, 1996, pp. 470-489, vol. 261, Issue 3, Elsevier, Amsterdam, Netherlands.

Ritchie et al., "Fast Computation, Rotation, and Comparison of Low Resolution Spherical Harmonic Molecular Surfaces", Proteins: Structure, Function, and Genetics, Mar. 1999, pp. 383-395 vol. 20, Issue 4, Wiley, Hoboken, NJ.

Robert et al., "Pembrolizumab versus Ipilimumab in Advanced Melanoma", N Engl J Med., Jun. 25, 2015, pp. 2521-2532, 372, Massachusetts Medical Society, Waltham, MA.

Selby et al., "Preclinical Development of Ipilimumab and Nivolumab Combination Immunotherapy: Mouse Tumor Models, In Vitro Functional Studies, and Cynomolgus Macaque Toxicology", PLoS One, Sep. 9, 2016, pp. 1-19, 11(9), PLoS One, San Francisco, CA.

Shimabukuro-Vornhagen et al., "Cytokine release syndrome", J Immunother Cancer, Jun. 15, 2018, pp. 14-14. 6, 56, BioMed Central Ltd., London, United Kingdom.

Sindel et al., "Hematopoietic stem cell mobilization following PD-1 blockade: Cytokine release syndrome after transplantation managed with ascorbic acid", Eur J Haematol., May 29, 2019, pp. 134-136, vol. 103, Issue 2, Wiley, Hoboken, NJ.

Souers et al., "ABT-199, a potent and selective BCL-2 inhibitor, achieves antitumor activity while sparing platelets", Nat. Med., Jan. 6, 2013, pp. 202-208, 19, Springer Nature, London , Germany.

Stank et al., "Protein Binding Pocket Dynamics", Acc. Chem. Res., Apr. 25, 2016, pp. 809-815, 49, ACS Publications, Washington, DC.

Still et al., "Semianalytical treatment of solvation for molecular mechanics and dynamics", J. Am. Chem. Soc., Aug. 1, 1990, pp. 6127-6129, vol. 112, American Chemical Society, Washington, D.C.

Stouten et al., "An effective solvation term based on atomic occupancies for use in protein sitnulations", Molecular Simulation, Sep. 23, 2006, pp. 97-120, vol. 10, No. 2-6, Gorden and Breach Science Publishers, New York, NY.

Tovar et al., "MDM2 small-molecule antagonist RG7112 activates p53 signaling and regresses human tumors in preclinical cancer models", Cancer Res. Apr. 2013, pp. 2587-2597, vol. 73, Issue 8, American Association for Cancer Research, Philadelphia, PA.

Wang et al., "TargetHunter: An In Silico Target Identification Tool for Predicting Therapeutic Potential of Small Organic Molecules Based on Chemogenic Database", The AAPS Journal, Jan. 5, 2013, pp. 395-406, 15(2), American Association of Pharmaceutical Scientists, Arlington, VA.

Wang et al., "Flexible ligand docking: A multistep strategy approach", Proteins, Jul. 1, 1999, pp. 1-19, vol. 36, Issue 1, Wiley, Hoboken, NJ.

Wang et al., "SCORE: A new empirical method for estimating the binding affinity of a protein-ligand complex", J. Molecular Modeling, 1998, pp. 379-394, vol. 4, Springer Nature, London , Germany.

Waszkowycz et al., "Large-scale virtual screening for discovering leads in the postgenomic era", IBM Systems Journal, 2001, pp. 360-376, vol. 40, No. 2, Thomson Reuters, Toronto, Ontario.

Welch et al., "Hammerhead: Fast, fully automated docking of flexible ligands to protein binding sites", Chemical Biology, 1996, pp. 449-462, vol. 3, Elsevier Inc., Amsterdam, Netherlands.

Wipf et al., "The Practice of Medicinal Chemistry" (Fourth Edition), Chapter 11, C. Wermuth et al., Eds, Academic Press, $4^{th}$ edition, pp. 279-299 (2015).

Yu et al., "Roll: a new algorithm for the detection of protein pockets and cavities with a rolling probe sphere", Bioinformatics, Jan. 1, 2010, pp. 46-52, vol. 26, Issue 1, Oxford Academic, Oxford, United Kingdom.

Zak et al., "Structure of the Complex of Human Programmed Death 1, PD-1, and its Ligand PD-L1", Structure, Dec. 1, 2015, pp. 2341-2348, vol. 23, Issue 12, Cell Press, Cambridge, MA.

Zhang et al., "Structural and functional analysis of the costimulatory receptor programmed death-1", Immunity, Mar. 2004, pp. 337-347, vol. 20, Issue 3, Elsevier Inc., Amsterdam, Netherlands.

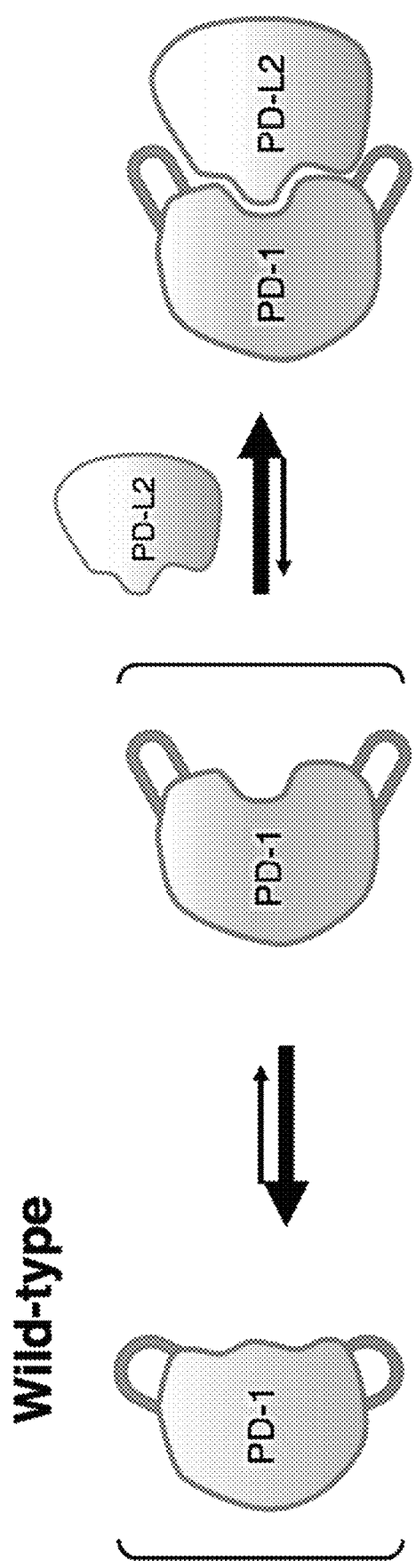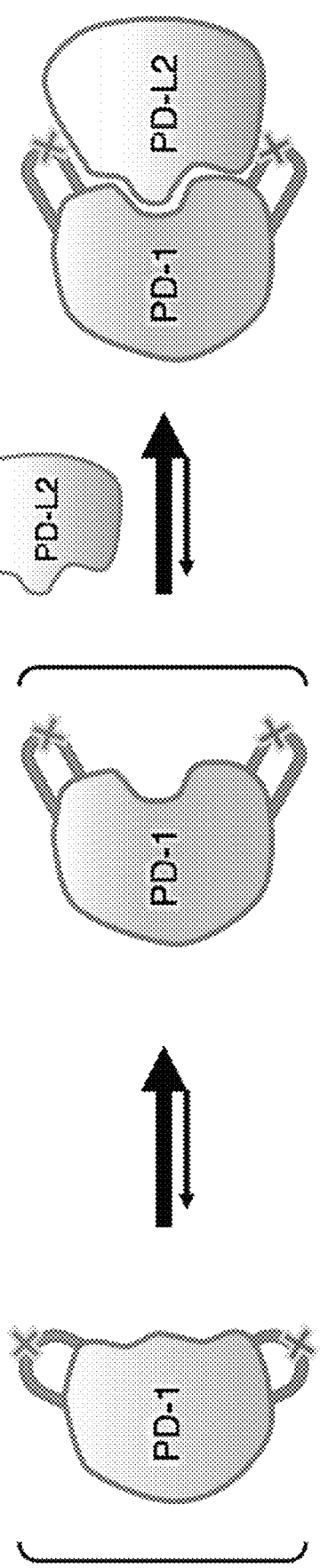
FIGURE 3A
FIGURE 3B

```
                          SEQUENCE LISTING

<160> NUMBER OF SEQ ID NOS: 4

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285

<210> SEQ ID NO 2
<211> LENGTH: 129
<212> TYPE: PRT
<213> ORGANISM: Artificial Sequence
<220> FEATURE:
<223> OTHER INFORMATION: Synthetic Construct
```

-continued

<400> SEQUENCE: 2

```
Met Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Val Leu Asn Trp Tyr Arg Met Ser Pro Ser Asn Gln Pro Asp Lys Leu
        35                  40                  45

Ala Ala Phe Pro Glu Asp Arg Ser Gln Pro Gly Gln Asp Ser Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Gly Ala Ile Ser
                85                  90                  95

Leu Ala Pro Lys Val Gln Ile Lys Glu Ser Leu Arg Ala Glu Leu Arg
            100                 105                 110

Val Thr Glu Arg Arg Ala Glu Gly Ser Trp Ser His Pro Gln Phe Glu
        115                 120                 125

Lys
```

<210> SEQ ID NO 3
<211> LENGTH: 140
<212> TYPE: PRT
<213> ORGANISM: Artificial Sequence
<220> FEATURE:
<223> OTHER INFORMATION: Synthetic Construct

<400> SEQUENCE: 3

```
Met Gly Trp Ser Cys Ile Ile Leu Phe Leu Val Ala Thr Ala Thr Gly
1               5                   10                  15

Val His Ser Asn Pro Pro Thr Phe Ser Pro Ala Leu Leu Val Val Thr
            20                  25                  30

Glu Gly Asp Ser Ala Thr Phe Thr Cys Ser Phe Ser Thr Ser Glu
        35                  40                  45

Ser Phe Val Leu Asn Trp Tyr Arg Met Ser Pro Ser Gly Gln Pro Asp
    50                  55                  60

Lys Leu Ala Ala Phe Pro Glu Asp Arg Ser Gln Pro Gly Gln Asp Ser
65                  70                  75                  80

Arg Phe Arg Val Thr Gln Leu Pro Asn Gly Arg Asp Phe His Met Ser
                85                  90                  95

Val Val Arg Ala Arg Arg Asp Asp Ser Gly Thr Tyr Leu Cys Gly Ala
            100                 105                 110

Ile Ser Leu Ala Pro Lys Val Gln Ile Lys Glu Ser Leu Arg Ala Glu
        115                 120                 125

Leu Arg Val Thr Glu Arg Arg Ala Glu Pro Glu Ala
    130                 135                 140
```

<210> SEQ ID NO 4
<211> LENGTH: 123
<212> TYPE: PRT
<213> ORGANISM: Artificial Sequence
<220> FEATURE:
<223> OTHER INFORMATION: Synthetic Construct

<400> SEQUENCE: 4

```
Met Ile Phe Leu Leu Leu Met Leu Ser Leu Glu Leu Gln Leu His Gln
1               5                   10                  15
```

```
Ile Ala Ala Leu Phe Thr Val Thr Val Pro Lys Glu Leu Tyr Ile Ile
            20              25              30

Glu His Gly Ser Asp Val Thr Leu Glu Cys Asn Phe Asp Thr Gly Ser
        35              40              45

His Val Asn Leu Gly Ala Ile Thr Ala Ser Leu Gln Lys Val Glu Asp
    50              55              60

Asp Thr Ser Pro His Arg Glu Arg Ala Thr Leu Leu Glu Glu Gln Leu
65              70              75              80

Pro Leu Gly Lys Ala Ser Phe His Ile Pro Gln Val Gln Val Arg Asp
            85              90              95

Glu Gly Gln Tyr Gln Cys Ile Ile Ile Tyr Gly Val Ala Trp Asp Tyr
            100             105             110

Lys Tyr Leu Thr Leu Lys Val Lys Ala Ser Tyr
        115             120
```

METHODS RELATED TO A STRUCTURE OF HIGH-AFFINITY HUMAN PD-1/PD-L2 COMPLEX

CROSS REFERENCE TO RELATED APPLICATION

This application claims the benefit of U.S. Provisional Application No. 62/904,515, filed Sep. 23, 2019, and U.S. Provisional Application No. 62/907,335, filed Sep. 27, 2019, both of which are incorporated by reference in its entirety herein.

STATEMENT AS TO RIGHTS TO INVENTIONS MADE UNDER FEDERALLY SPONSORED RESEARCH AND DEVELOPMENT

This invention was made with Government support under Contracts DA043893 and GM103393 awarded by the National Institutes of Health and DE-AC02-76F00515 awarded by the U.S. Department of Energy. The government has certain rights in the invention.

BACKGROUND

Immune checkpoint blockade of programmed death 1 (PD-1) and its ligand 1 (PD-L1) has dramatically increased progression-free survival for many cancers (1-3). For example, a monoclonal antibody (mAb) drug, pembrolizumab (Keytruda®), received regulatory approval for use in patients with microsatellite instability-high (MSI-H) or mismatch repair deficient (dMMR) solid tumors (4, 5). While mAb drugs inhibiting immune checkpoints are highly useful in oncology, there is a desire for other types of inhibitors of of immune checkpoints, such as small-molecules. Small-molecule drugs targeting PD-1 may lead to increases in efficacy and safety of cancer treatment, as well to improved access to cancer treatments.

SUMMARY

Other than mAbs, compounds targeting human PD-1 so far have been out of reach. Development of human PD-1-binding drugs is hindered by the fact that the ligand-binding surface of human PD-1 is generally flat, lacking identifiable binding pockets that can serve as drug targets during computational screening of small molecule libraries and computational drug modelling efforts. Only a small cavity forms when human PD-1 binds one of its in-vivo ligands, PD-L1. The small volume of the PD-L1 binding cavity in human PD-1 prevents its use for computational modelling of PD-1 interactions with its ligands. While it is known that, in murine PD-1, the PD-L1-binding cavity extends upon binding of a different in-vivo ligand, PD-L2, the cavity of murine PD-1 cannot provide a structural model due to low sequence similarity between human and murine PD-1 proteins. As described in more detail further in the present disclosure, the inventors were able to design a substituted variant of human PD-1 that binds PD-L2 with an affinity that is two orders of magnitude higher than that of the wild-type protein, and to crystallize and, using X-ray crystallography, determine to high resolution the structures of the human PD-1 variant and the complex of the human PD-1 variant with PD-L2. As a result, a prominent pocket on the ligand-binding surface of human PD-1 was identified. The structure of the PD-L2 binding pocket of human PD-1 is described in the present disclosure. The structure of the PD-L2 binding pocket of human PD-1 is useful, for example, in the drug discovery, design and optimization methods, such as, but not limited to, the methods that involve computational (in silico) screening of small molecule libraries for candidate small molecules capable of binding to of the PD-L2 binding pocket of human PD-1, the methods that involve computational identification of ligands capable of interacting with the PD-L2 binding pocket of human PD-1, and any methods that involve computational docking of ligands to the PD-L2 binding pocket of human PD-1. Such methods are included among the embodiments of the present invention and are described in the present disclosure.

The terms "invention," "the invention," "this invention" and "the present invention," as used in this document, are intended to refer broadly to all of the subject matter of this patent application and the claims below. Statements containing these terms should be understood not to limit the subject matter described herein or to limit the meaning or scope of the patent claims below. Covered embodiments of the invention are defined by the claims, not this summary. This summary is a high-level overview of various aspects of the invention and introduces some of the concepts that are described and illustrated in the present document and the accompanying figures. This summary is not intended to identify key or essential features of the claimed subject matter, nor is it intended to be used in isolation to determine the scope of the claimed subject matter. The subject matter should be understood by reference to appropriate portions of the entire specification, any or all figures and each claim. Some of the exemplary embodiments of the present invention are discussed below.

Included among the embodiments of the present invention are proteins comprising a ligand binding pocket with a three-dimensional structure corresponding to a structure of PD-L2 binding pocket of a variant of human PD-1 with one or more of amino acid substitutions in residues corresponding to N74, T76 or A132 of SEQ ID NO:1. A variant of human PD-1 can further comprises amino acid substitutions removing one or more N-linked glycosylation sites. In a protein according to the embodiments of the present invention, the one or more of the amino acid substitutions are two or three amino acid substitutions. The amino acid substitutions can be N74G, T76P or A132V. The amino acid substitutions can be N74G, T76P, A132V or A132L. A protein according to the embodiments of the present invention can comprise amino acid substitutions N74G, T76P and A132L. A protein according to the embodiments of the present invention amino acid substitutions N74G and A132V. A protein according to the embodiments of the present invention can be a variant of human PD-1. In a protein according to the embodiments of the present invention, the PD-L2 binding pocket of the variant of human PD-1 can include bound PD-L2. In a protein according to the embodiments of the present invention, a ligand binding pocket can form upon binding of a non-PD-L2 ligand to the protein. The non-PD-L2 ligand can be a small-molecule ligand. In a protein according to the embodiments of the present invention, a binding pocket can exist in the absence of a bound ligand. Embodiments of the present invention encompass crystal forms of the proteins described in the present disclosure.

Also included among the embodiments of the present invention are variants of human PD-1, wherein the variant of human PD-1 comprising one or more of amino acid substitutions in residues corresponding to N74, T76 and A132 of SEQ ID NO: 1. A variant of human PD-1 can be in crystal form. A variant of human PD-1 according to the embodiments of the present invention can include two or three amino acid substitutions. The amino acid substitutions can be N74G, T76P or A132V. In an exemplary embodiment, a variant of human PD-1 includes amino acid substitutions N74G, T76P and A132L. In another exemplary embodiment, a variant of human PD-1 includes amino acid substitutions N74G and A132V. A variant of human PD-1 can further include amino acid substitutions removing one or more N-linked glycosylation sites. A variant of human PD-1 can be capable of binding PD-L2 or be bound to PD-L2.

Also included among the embodiments of the present invention are methods for identifying a small molecule capable of binding to PD-L2 binding pocket of human PD-1. A method according to the embodiments of the present invention can comprise the steps of: I) screening small molecule libraries using in silico docking for candidate small molecules that are identified based on a docking score being above a threshold for binding to a binding pocket with a three-dimensional structure corresponding to a structure of the PD-L2 binding pocket of human PD-1; and II) evaluating the candidate small molecules identified in step (I) through one or more in vitro or in vivo assays for their ability to bind to surface residues of the PD-L2 binding pocket of human PD-1 to thereby identify the small molecule capable of binding to the PD-L2 binding pocket of human PD-1. In a method, the candidate small molecules can be identified as binding with the PD-L2 binding pocket of human PD-1 via the docking score that includes one or more interactions of (a) to (k): a) the candidate small molecules interact via hydrogen bonds with one or more amino acid residues in the PD-L2 binding pocket of human PD-1; b) the candidate small molecules interact via hydrogen bonds with the PD-L2 binding pocket of human PD-1; c) the candidate small molecules interact via ionic interactions with one or more amino acid residues in the PD-L2 binding pocket of human PD-1; d) the candidate small molecules interact via ionic interactions with the PD-L2 binding pocket of human PD-1; e) the candidate small molecules interact via one or more water molecules with one or more amino acid residues in the PD-L2 binding pocket of human PD-1; f) the candidate small molecules interact via one or more water molecules with the PD-L2 binding pocket of human PD-1; g) the candidate small molecules interact via π-π interactions with one or more amino acid residues in the in the PD-L2 binding pocket of human PD-1; h) the candidate small molecules interact via van der Waals interactions to one or more amino acid residues in the in the PD-L2 binding pocket of human PD-1; i) the candidate small molecules interact via van der Waals interactions with the PD-L2 binding pocket of human PD-1; j) the candidate small molecules interact via steric interactions to one or more amino acid residues in the in the PD-L2 binding pocket of human PD-1; k) the candidate small molecules interact via steric interactions with the PD-L2 binding pocket of human PD-1. In some embodiments, the candidate small molecules are not endogenous ligands of human PD-1. In some embodiments, the candidate small molecules have 1, 2, 3, 4, 5, 6, 7, 8, 9, 10 or 11 of the interactions (a)-(k). In some embodiments, the candidate small molecules bind via 1-20 hydrogen bonds to one or more amino acid residues in the PD-L2 binding pocket of human PD-1. In some embodiments, the candidate small molecules bind via 1-20 hydrogen bonds to the PD-L2 binding pocket of human PD-1. In some embodiments, the candidate small molecules bind via 1-20 water molecules in the PD-L2 binding pocket of human PD-1. In some embodiments, the candidate small molecules bind via 1-20 water molecules to one or more amino acid residues in the PD-L2 binding pocket of human PD-1. In some embodiments, a model of the structure of the PD-L2 binding pocket of human PD-1 is computationally derived from crystallographic data. In some embodiments, model of the PD-L2 binding pocket of human PD-1 is computationally derived from crystallographic data obtained using crystals of a variant of human PD-1 according to the embodiments of the present invention and described elsewhere in the present disclosure. In some embodiments of the methods, in silico docking comprises computational docking three-dimensional structures of small molecules from the small molecule libraries onto surface exposed amino acid residues of the model of the PD-L2 binding pocket of human PD-1. In some embodiments, the surface exposed amino acid residues comprise one or more amino acids corresponding to F63, V64, N66, Y68, E84, L122, I126, I134 or E136 of SEQ ID NO: 1. In some embodiments, the computational docking comprises sampling, scoring, and binning of docking scores of a plurality of docked orientations of the small molecules relative to the model of the PD-L2 binding pocket of human PD-1. In some embodiments, the computation docking further comprising assigning a distance cutoff to match atoms of the small molecules to exposed atoms of the PD-L2 binding pocket of human PD-1. The exposed atoms can include one or more of CB of F63, CE1 of F63, CD1 of F63, CE1 of F63, CG2 of V64, CG2 of V64, O of V64, ND2 of N66, ND2 of N66, CE1 of Y68, OH of Y68, OE1 of E84, OE2 of E84, OE2 of E84, OE1 of E84, OE2 of E84, OE1 of E84, CD1 of L122, CG2 of I126, CD1 of I126, CD1 of I126, CG2 of I126, CD1 of I126, CB of I134, CG1 of I134, CG1 of I134, CD1 of I134, CD1 of I134, OE2 of E136, OE2 of E136 or OE2 of E136, wherein numbering of amino acids containing the exposed atoms is based on SEQ ID NO: 1. In some embodiments, the scoring comprises determining, for complexes of the small molecules and the PD-L2 binding pocket of human PD-1, one or more of binding forces, configurational entropy, local minimal in Gibbs free energy landscape, or energy barriers between the local minima of the Gibbs free energy landscape, or combinations of two or more thereof.

Also described herein and included among the embodiments of the present invention are in silico method of identifying a compound that binds to PD-L2 binding pocket of human PD-1. The methods can comprise the steps of: (a) receiving, by a computer system, information on a three-dimensional structure of PD-L2 binding pocket of human PD-1 comprising a plurality of amino acids; (b) receiving, by the computer system, information on a three-dimensional structure of a candidate compound; (c) using the computer system and the information received into the computer system in steps (a) and (b), performing one or more of molecular dynamic simulations, kinetic Monte Carlo (KMC) simulations, direct simulations Monte Carlo (DSMC), or density functional theory (DFT) simulations to determine if the candidate compound binds to the PD-L2 binding pocket of human PD-1, thereby identifying the compound that binds to PD-L2 binding pocket of human PD-1. In the above methods, the three-dimensional structure of the PD-L2 binding pocket of human PD-1 can be computationally derived from crystallographic data. The crystallographic data can be obtained using crystals of a variant of human PD-1 according to the embodiments of the present invention and described elsewhere in the present disclosure. In a method according to the embodiments of the present invention, step (c) can include computational docking of small molecules from small molecule libraries onto surface exposed amino acid residues of the three-dimensional structure of the PD-L2 binding pocket of human PD-1. The surface exposed amino acid residues can include one or more amino acids corresponding to F63, V64, N66, Y68, E84, L122, I126, I134 or E136 of SEQ ID NO: 1. In a method according to the embodiments of the present invention, step (c) can include determining, using the computer system, a docking score of the candidate compound to the PD-L2 binding pocket of human PD-1. The determining of the docking score can include sampling, scoring and binning of docking scores of a plurality of docked orientations of the small molecules relative to the model of the PD-L2 binding pocket of human PD-1, and assigning a distance cutoff to match atoms of the small molecules to exposed atoms of the PD-L2 binding pocket of human PD-1. The exposed atoms can include one or more of CB of F63, CE1 of F63, CD1 of F63, CE1 of F63, CG2 of V64, CG2 of V64, O of V64, ND2 of N66, ND2 of N66, CE1 of Y68, OH of Y68, OE1 of E84, OE2 of E84, OE2 of E84, OE1 of E84, OE2 of E84, OE1 of E84, CD1 of L122, CG2 of I126, CD1 of I126, CD1 of I126, CG2 of I126, CD1 of I126, CB of I134, CG1 of I134, CG1 of I134, CD1 of I134, CD1 of I134, OE2 of E136, OE2 of E136 or OE2 of E136, wherein numbering of amino acids containing the exposed atoms is based on SEQ ID NO: 1. In a method according to the embodiments of the present invention, step (c) can include determining, for the complexes of the compound and the PD-L2 binding pocket of human PD-1, one or more of binding forces, configurational entropy, local minimal in Gibbs free energy landscape or energy barriers between the local minima of the Gibbs free energy landscape, or combinations of two or more thereof.

Also included among the embodiments of the present invention are methods for identifying interactions between a ligand and a PD-L2 binding pocket of human PD-1. A method according to the embodiments of the present invention cam comprise the steps of: (a) receiving, by a computer system, test ligand molecular data corresponding to a test ligand that is a candidate drug; (b) receiving, by the computer system, protein molecular data corresponding to a three-dimensional structure of PD-L2 binding pocket of human PD-1; (c) calculating an interaction score between the PD-L2 binding pocket of human PD-1 and the candidate drug. In A method according to the embodiments of the present invention can further comprise a step of comparing the interaction score to a threshold score to determine whether or not an interaction exists between the PD-L2 binding pocket of human PD-1 and the candidate drug. An interaction score can be determined for each of a plurality of test ligands, including the test ligand, and the method can further comprise the steps of: determining a ranking the plurality of the interactions scores; and comparing the ranking of the test ligand to a threshold to determine whether or not an interaction exists between the PD-L2 binding pocket of human PD-1 and the candidate drug. In a method according to the embodiments of the present invention, step (c) can include performing one or more of molecular dynamic simulations, kinetic Monte Carlo (KMC) simulations, direct simulations Monte Carlo (DSMC), or density functional theory (DFT) simulations, or combinations of two or more thereof. In a method according to the embodiments of the present invention, step (c) can include determining, for the complexes of the test ligand and the PD-L2 binding pocket of human PD-1, one or more of binding forces, configurational entropy, local minimal in Gibbs free energy landscape, or energy barriers between the local minima of the Gibbs free energy landscape. In a method according to the embodiments of the present invention, the three-dimensional structure of the PD-L2 binding pocket of human PD-1 is computationally derived from crystallographic data. The crystallographic data can be obtained using crystals of a variant of human PD-1 according to the embodiments of the present invention and described elsewhere in the present disclosure. In a method according to the embodiments of the present invention, step (c) can include computational docking of small molecules from the small molecule libraries onto surface exposed amino acid residues of the model of the PD-L2 binding pocket of human PD-1. The surface exposed amino acid residues can comprise one or more amino acids corresponding to F63, V64, N66, Y68, E84, L122, I126, I134 or E136 of SEQ ID NO: 1. In a method according to the embodiments of the present invention, step (c) can include determining, using the computer system, a docking score of the candidate compound to the PD-L2 binding pocket of human PD-1. The determining of the docking score can include sampling, scoring and binning of docking scores of a plurality of docked orientations of the small molecules relative to the model of the PD-L2 binding pocket of human PD-1, and assigning a distance cutoff to match atoms of the small molecules to exposed atoms of the PD-L2 binding pocket of human PD-1. The exposed atoms can include one or more of CB of F63, CE1 of F63, CD1 of F63, CE1 of F63, CG2 of V64, CG2 of V64, O of V64, ND2 of N66, ND2 of N66, CE1 of Y68, OH of Y68, OE1 of E84, OE2 of E84, OE2 of E84, OE1 of E84, OE2 of E84, OE1 of E84, CD1 of L122, CG2 of I126, CD1 of I126, CD1 of I126, CG2 of I126, CD1 of I126, CB of I134, CG1 of I134, CG1 of I134, CD1 of I134, CD1 of I134, OE2 of E136, OE2 of E136 or OE2 of E136, wherein numbering of amino acids containing the exposed atoms is based on SEQ ID NO:1.

In some embodiments of the methods described in the present disclosure, a candidate compound, such as a candidate small molecule, can be a candidate anti-cancer drug. The methods can therefore include testing the candidate anti-cancer drug in an in vitro or in vivo assay to determine its anti-cancer efficacy. The methods can also include determining toxicity of the candidate anti-cancer drug. The methods can also include determining if the candidate anti-cancer drug has an off-target effect. The toxicity or the off-target effect can be determined by an in vitro assay, by an in vivo assay, in silico, or by a combination of two or more thereof. The methods can also include optimizing the candidate anti-cancer drug. For example, the candidate anti-cancer drug can be optimized to one or more of: reduce an off-target effect, reduce toxicity, increase or decrease binding affinity for the PD-L2 binding pocket of human PD-1, decrease binding affinity for the PD-L2 binding pocket of human PD-1. Also included among the embodiments of the present invention are computer products comprising a non-transitory computer readable medium storing a plurality of instructions that when executed control a computer system to identity protein-drug interactions by performing the methods according to the embodiments of the present invention.

BRIEF DESCRIPTION OF THE FIGURES

FIG. 1A shows a space-filling and ribbon diagram overlay of the human PD-1$^{N74G\ T76P\ A132V}$ (dark grey)/PD-L2$^{IgV}$ (light grey)), showing the overall architecture of the human PD-1/PD-L2 complex. FIG. 1B shows a ribbon diagram of a ~180° rotation view of the ribbon diagram shown in FIG. 1A. Substitutions of N74G, T76P, and A132V are labeled and their sidechains are indicated with sticks. The β-sheets on the interacting faces of each protein are labeled.

FIGS. 2A and 2B show the close-up views of space-filling models of apo-human PD-1$^{N74G\ T76P\ A132V}$ (FIG. 2A), and human PD-L2-bound human PD-1$^{N74G\ T76P\ A132V}$ overlaid with pocket-residues in sticks (FIG. 2B). The pocket shown in FIG. 2B adopts a funnel-shaped architecture (left: entrance, and right: end) with a volume measured as 130 Å$^3$. FIG. 2C shows a space-filling models of pockets of human PD-L2-bound human PD-1$^{N74G\ T76P\ A132V}$ with a ribbon diagram of the 3G of PD-L2. The PD-L2 interacting-residues are overlaid in sticks and labeled with an L2 subscript. A 130 Å$^3$ funnel-shaped pocket (left, entrance; right, exit) when human PD-1 binds PD-L2

FIGS. 3A and 3B schematically illustrate a model for conformational coupling for PD-L2 binding to PD-1. Schematic cartoon model shown in FIG. 3A is that of human PD-1 with a flat interface (left) in equilibrium with the PD-L2-bound conformation in the absence of PD-L2 (middle). Schematic cartoon model shown in FIG. 3B is that of the PD-1 loop variant with increased population of the PD-L2-bound conformations in the absence of PD-L2. For clarity, only two of the states in the conformational ensembles are depicted in the schematic cartoon models. Crosses indicate the loop substitutions. Binding of PD-L2 stabilizes the bound conformation of PD-1 (right).

FIGS. 4A and 4B show ribbon diagrams of human PD-1/PD-L2 interface overlaid with interacting residues in sticks. ~180° rotation between views shown in FIGS. 4A and 4B.

FIGS. 5A and 5B show close-up ribbon diagrams of the localizations of the loop substitutions overlaid in sticks of the mutated G74, P76 (FIG. 5A), and V132 (FIG. 5B) in the human PD-1/PD-L2 structure. The PD-L2 residues are overlaid in sticks and labeled with an L2 subscript. P76 of the CC' loop of PD-1 localizes in between sidechains of Y112$_{L2}$ and Y114$_{L2}$. V132 of the FG loop localizes to a groove of T56$_{L2}$ S58$_{L2}$ I103$_{L2}$ and I105$_{L2}$. FIGS. 5C and 5D show close-up ribbon diagrams of the localizations of the loop substitutions overlaid in sticks of N74, T76 (FIG. 5C), and A132 (FIG. 5D) in the human PD-1/PD-L1 structure (PDB: 4ZQK). The PD-L1 residues are overlaid in sticks and labeled with an L1 subscript. Compared to PD-L2, the corresponding Y114$_{L2}$ is substituted by R125$_{L1}$. A132 of the FG loop localizes to a groove of I54$_{L1}$, Y56$_{L1}$, Q66$_{L1}$, and M115$_{L1}$ in PD-L1.

DETAILED DESCRIPTION

Figures 1A, 1B:
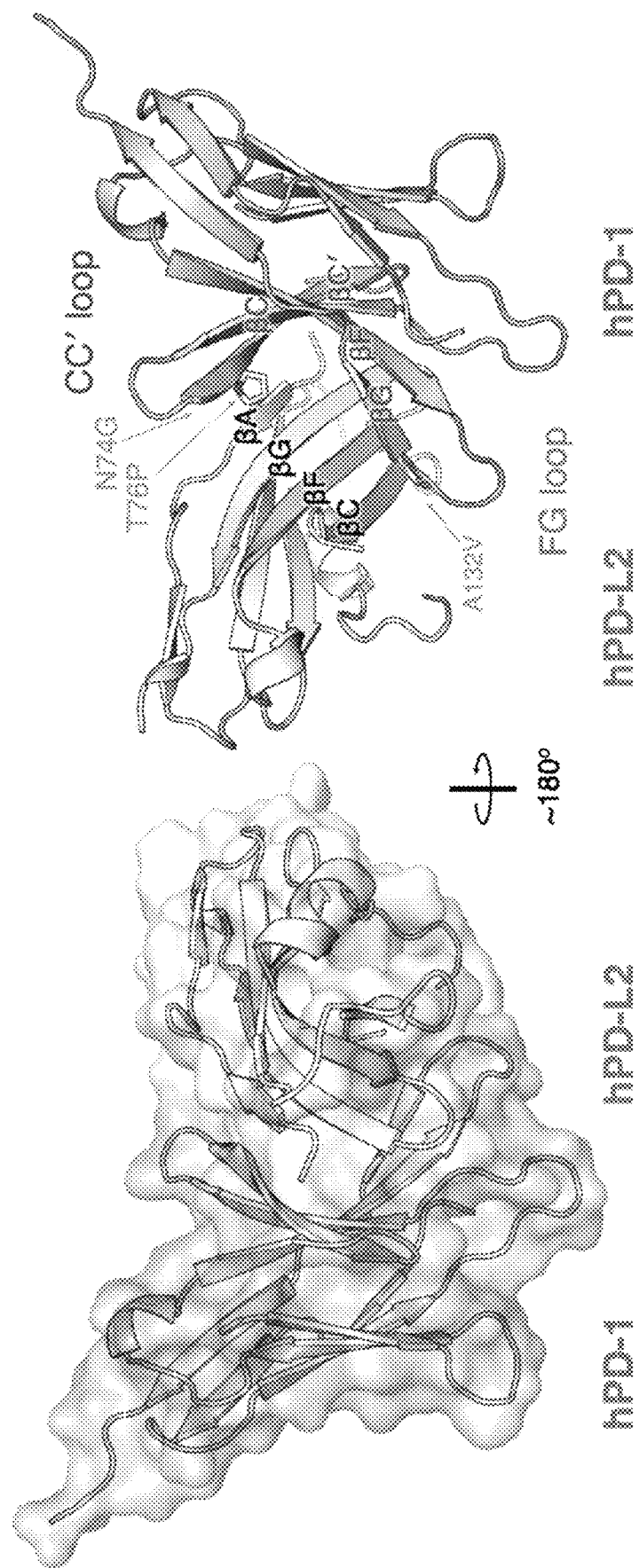
FIGS. 1A and 1B schematically illustrates the X-ray crystal structure of the human PD-1/PD-L2 complex.

PD-1 is a receptor expressed by T cells, B cells, and monocytes, and is a potent regulator of immune responses (16). PD-1 is an attractive target for anti-cancer pharmaceuticals. PD-1 has two known protein ligands in vivo, PD-L1 and PD-L2, which bind to the same region on the surface of PD-1. It would be desirable to identify other ligands, including, but not limited to small molecule compounds, that would bind to this region of human PD-1 and interfere with its binding to PD-L1 and/or PD-L2. Such ligands, once identified, may be used as lead compounds for drug development and tested for potential biological activity, such as anti-cancer activity, by suitable in vitro and/or in vivo assays. However, it is currently impossible to identify in silico the ligands that would specifically and efficiently bind to PD-1 ligand-binding site, because the PD-1 ligand-binding site lacks a defined binding pocket in the absence of its in vivo ligands. Although the structure of human PD-1/PD-L1 complex has been determined, and a model of PD-L1 binding cavity of human PD-1 exists, the volume of PD-1 binding cavity in the above model is too small for the model to be used effectively in computational studies of PD-1/ligand interactions. As a consequence, until the discoveries described in the present disclosure, effective computational of PD-1/ligand interactions were intractable, making it impossible, for example, to pre-select a reasonable number of lead ligands, such as small-molecule compounds for further testing with in vitro and/or in vivo assays for PD-1 signaling in order to identify biologically active ligands that can be used as drug candidates in pre-clinical and/or clinical testing. The absence of a model of binding PD-1/PD-L1 binding cavity also prevented in silico rational drug design and optimization studies.

The available structures of murine PD-1/PD-L1 and PD-1/PD-L2 complexes showed that a modest binding cavity was formed upon PD-L1 binding, and the cavity extended to a volume suitable for small-molecule ligands only upon PD-L2 binding to murine PD-1. However, the model of the structure of murine PD-1/PD-L2 complex is unsuitable for human drug development due to low sequence similarity between the human and murine PD-1 proteins. Since human PD-1 protein has a very mobile structure, all the multiple previous attempts to crystalize human PD-1/PD-L2 complex and determine the structure of PD-1 ligand binding pocket failed. As described in the present disclosure, the inventors were able to stabilize the structure of PD-1/PD-L2 complex by mutating several residues in two mobile loops (CC' and FG) of PD-1, which increased the affinity of PD-1 for PD-L2. The inventors were then able to crystallize the PD-1/PD-L2 complex and determine the structure of the PD-L2 binding pocket. The model of the structure of human PD-1/PD-L2 binding pocket can now be used for drug discovery and development. One non-limiting example of the drug discovery and development process in which the structure of human PD-1/PD-L2 binding pocket can be used, is a process that involves computational screening of compounds to identify PD-1 ligands ("leads"). In the above process, screened compounds can be small molecules. For example, libraries of small compounds (small-molecule libraries) can be computationally screed according to various procedures, some of which are described in the present disclosure, to identify candidate small molecules capable of binding to a PD-L2 binding pocket of human PD-1. Based on the results of the computational screening, potential leads can be tested by appropriate in vitro and/or in vivo testing to identify the compounds that affect PD-1 signaling. Another non-limiting example in which the structure of human PD-1/PD-L2 binding pocket can be used is a process that involves computational design and testing of candidate ligands ("leads"), which can subsequently be tested by appropriate in vitro and/or in vivo testing to identify the compounds that affect PD-1 signaling. Prior to the determination of the structure, described in the present disclosure, of human PD-1/PD-L2 binding pocket, it was impossible to identify computationally (in silico) the leads for subsequent in vitro and/or in vivo testing identify the compounds that affect PD-1 signaling. Although in vitro and/or in vivo testing without prior in silico lead identification was theoretically possible, it was, in practice, unworkable due to the high costs (including monetary, time, labor and animal lives required for the testing) that would be required to test large numbers of essentially randomly selected compounds with low probability of success. The discoveries described in the present disclosure permit carrying out the processes related to drug discovery, such as, but not limited to, screening of small molecules and rational drug design, in which in vitro and/or in vivo testing of lead compounds can be implement practically and effectively due to the now available capability to perform the initial steps of lead screening and/or design computationally, thereby drastically reducing the number of the leads that need to be tested in vitro and/or in vivo to identify biologically active PD-1 ligands that can serve as drug candidates in subsequent pre-clinical and clinical testing.

```
An exemplary amino acid sequence of human PD-1
(SEQ ID NO: 1), UniProt database entry Q15116
       10         20         30         40
MQIPQAPWPV VWAVLQLGWR PGWFLDSPDR PWNPPTFSPA 50         60         70         80
LLVVTEGDNA TFTCSFSNTS ESEVLNWYRM SPSNQTDKLA 90        100        110        120
AFPEDRSQPG QDCRFRVTQL PNGRDFHMSV VRARRNDSGT 130        140        150        160
YLCGAISLAP KAQIKESLRA ELRVTERRAE VPTAHPSPSP 170        180        190        200
RPAGQFQTLV VGVVGGLLGS LVLLVWVLAV ICSRAARGTI 210        220        230        240
GARRTGQPLK EDPSAVPVFS VDYGELDFQW REKTPEPPVP 250        260        270        280
CVPEQTEYAT IVFPSGMGTS SPARRGSADG PRSAQPLRPE

DGHCSWPL
```

An exemplary amino acid sequence of human PD-1 protein is shown as SEQ ID NO: 1. The present disclosure describes, among other things, structures of the human triple-mutant PD-1/PD-L2 complex and the apo triple-mutant PD-1 variant obtained using X-ray crystallography at 2.0 Å and 1.2 Å resolution, respectively. The structures described in the present disclosure revealed that binding of PD-L2 to human PD-1 was accompanied by formation of a prominent pocket in human PD-1, as well as substantial conformational changes of the CC' and FG loops. The structure of human apo triple-mutant PD-1 revealed that the CC' loop adopted the ligand-bound conformation, providing support for allostery between the loop and pocket. The structures of human PD-1/PD-L2 described in the present disclosure are useful for design and discovery of small-molecule PD-1 inhibitors. While mAb drugs inhibiting immune checkpoints, such as pembrolizumab, are highly useful in oncology, small-molecule inhibitors of immune checkpoints are highly desirable. Small molecule inhibitors are expected to penetrate more effectively than mAbs in the tumor microenvironment, which can enhance their efficacy (6). In addition, if penetration into the brain is desired, small molecule inhibitors can be effective (7, 8). Also, there are rare but severe immune-related side effects of checkpoint inhibition that call for immediate drug discontinuation (9, 10). Since mAbs have long half-lives in the body (typically, weeks) (11), the treatment of such severe immune-related side effects is primarily supportive. Small-molecule checkpoint inhibitors can offer the potential for convenient dosing (e.g., once a day), while allowing for prompt drug removal, if desired (12). Small-molecule immune checkpoint inhibitors can facilitate treatment of cancers in low- and middle-income countries by reducing production costs and eliminating the need for refrigeration during transportation and storage, as compared to mAbs (13). Despite substantial efforts, currently there are no well-characterized small-molecule ligands for PD-1 (14, 15).

In vivo, PD-1 binds two distinct ligands, PD-L1 (also known as B7-H1 or CD274) and PD-L2 (also known as B7-DC) (16). The ligand-binding surface of human PD-1 is generally flat, lacking pockets considered suitable for binding small molecules (16). However, upon binding to PD-L1, a modest cavity forms on the ligand binding surface of PD-1 (17). A similar cavity is formed in murine PD-1 upon binding PD-L1 (18). When murine PD-1 binds PD-L2 (19), this cavity extends to a volume comparable to that occupied by established small-molecule inhibitors (20, 21). Unfortunately, currently available structure of murine PD-1/PD-L2 complex is insufficient to provide a structural model for the analogous pocket in the human PD-1/PD-L2 complex, as the human and murine PD-1 proteins share sequence identities of only about 63% (22). Although the structure of murine PD-1/PD-L2 complex was determined over a decade ago, the structure of the human complex has not yet been obtained due to various difficulties. Previous attempts to obtain diffraction-quality crystals of human PD-1/PD-L2 complex were unsuccessful.

The inventors realized that formation of cavities on the ligand-binding surface of PD-1 is accompanied by changes in the structures of the CC' and FG loops. The inventors further realized that substitutions in these loops can have an allosteric effect on the conformations of PD-1 in the pocket region and alter its affinity for PD-L2. Using deep-mutational scanning (24) and yeast-surface display (25), the CC' and FG loop variants of human PD-1 with enhanced PD-L2 binding were selected. A triple-mutant PD-1 was identified that binds PD-L2 with nanomolar affinity and is amenable to crystallization, both alone and as a complex. The formation of a prominent pocket in human PD-1 upon binding PD-L2 revealed by the X-ray crystal structures described in the present disclosure supports the notion of allostery between the pocket and the CC' and FG loops. The pocket identified in human PD-1 can serve as a template for virtual drug discovery (26) and opens up additional avenues for the discovery of small-molecule PD-1 inhibitors.

Figures 2A, 2B, 2C:
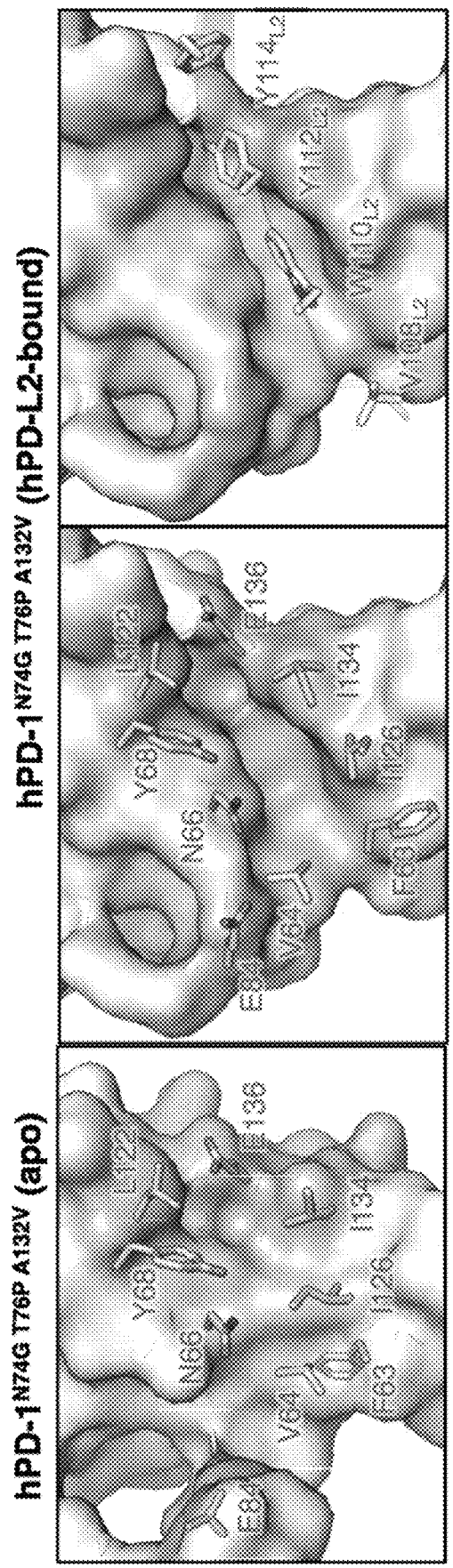
FIGS. 2A, 2B and 2C schematically illustrate the formation of a prominent pocket in human PD-1 upon binding PD-L2.

The prominent pocket formed in human PD-1 upon binding PD-L2 has a volume of 130 Å$^3$, comparable to those pockets that bind small-molecule drugs (20, 21, 35). The structure of the pocket in human PD-1 described in the present disclosure is quite distinct from the corresponding pocket in murine PD-1 when bound to PD-L2 (19). The pocket in human PD-1 described in the present disclosure represents an attractive drug target. It is envisioned that a small molecule binding to PD-1 contacting all or many of the residues that form the pocket, particularly F63, V64, N66, Y68, E84, L122, G124, I126, I134, and E136 in a conformation similar to that formed in the complex with PD-L2, as illustrated in FIG. 2B. The structure of human PD-1/PD-L2 complex is useful for virtual drug screening to identify potential lead compounds (see e.g., (26)). In addition, the structures of the indole and phenyl rings and neighboring sidechains of PD-L2 when bound to the pocket, as illustrated in FIG. 2C, are useful for the design of fragment-based screening scaffolds (36, 37).

Conformational changes in the CC' and FG loops can be coupled to formation of pockets in the ligand-binding interface of PD-1 (FIG. 3). In this model, PD-1 exists in an ensemble of conformations in the absence of ligands, populating predominantly structures containing a flat ligand-binding face ($K_1<1$). PD-1 molecules with a pre-formed pocket have a higher affinity for PD-L2 (i.e., $K_3>K_2$). Thermodynamics dictates that $K_1K_3=K_2K_4$, so $K_4>K_1$. In this model, the PD-1 loop variants studied here increase $K_1$, and lead to a higher proportion of apo-PD-1 in the PD-L2-bound conformation. The increased association constants ($k_{on}$) for binding ligands by the mutant PD-1s, as compared to wild-type PD-1 support this model. Such kinetic properties are consistent with an increase fraction of unliganded mutant PD-1 molecules that are in a ligand-bound conformation as compared to wild-type PD-1 (38, 39). In addition, the CC' loop shifts toward the PD-L2-bound conformation in the apo-PD-1 triple and double mutants. While there are only minimal changes in the pocket of human PD-1, as illustrated in FIG. 2A, the pocket residues and a neighboring FG loop have substantial crystal contacts in the lattice that likely interfere with conformational changes. Such coupling can stabilize the pocket in the absence of a ligand, for example, if the two loops were held in their PD-L2-bound conformations with antibodies or aptamers. Thus, the structures of human PD-1 described in the present disclosure are useful in drug development, such as, but not limited to, small-molecule drug discovery, such as by high-throughput screening (40, 41), and rational drug design. The structures described in the present disclosure can be used to discover, design and/or optimize PD-1 ligands, including small-molecule ligands, and can also be used in the discovery of allosteric regulators of PD-1 activity.

Terms and Concepts

A number of terms and concepts are discussed below. They are intended to facilitate the understanding of various embodiments of the invention in conjunction with the rest of the present document and the accompanying figures. These terms and concepts may be further clarified and understood based on the accepted conventions in the fields of the present invention. the description provided throughout the present document and/or the accompanying figures. Some other terms can be explicitly or implicitly defined in other sections of this document and in the accompanying figures, and may be used and understood based on the accepted conventions in the fields of the present invention, the description provided throughout the present document and/or the accompanying figures. The terms not explicitly defined can also be defined and understood based on the accepted conventions in the fields of the present invention and interpreted in the context of the present document and/or the accompanying figures.

Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry are those well-known and commonly used. Known methods and techniques are generally performed according to conventional methods well known and as described in various general and more specific references that are discussed throughout the present disclosure, unless otherwise indicated. For example, enzymatic reactions and purification techniques are performed according to manufacturer's specifications, as commonly accomplished. The nomenclatures used in connection with the laboratory procedures and techniques described in the present disclosure are those well-known and commonly used.

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile), leucine (Leu), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). In the broadest sense, the naturally occurring amino acids can be divided into groups based upon the chemical characteristic of the side chain of the respective amino acids. By "hydrophobic" amino acid is meant either His, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further sub-classed as follows: by "uncharged hydrophilic" amino acid is meant either Ser, Thr, Asn or Gln. By "acidic" amino acid is meant either Glu or Asp. By "basic" amino acid is meant either Lys, Arg or His.

The term "variant," when used in the present disclosure in reference to a protein or a polypeptide, encompasses homologues, variants, isoforms, fragments, mutants, modified forms and other variations of the protein, polypeptide or amino acid sequences described in this document. The term "homologous," "homologues" and other related terms used in this document in reference to various amino acid, are intended to describe a degree of sequence similarity among amino acid sequences, calculated according to an accepted procedure. Homologous sequences may be at least 60%, 65%, 70%, 75%, 80%, 85%, 90%, 91%, 92%, 93%, 94%, 95%, 96%, 97%, 98% 99% or 100% homologous. As used herein, "percent homology" of two amino acid sequences is determined using the algorithm of Karlin and Altschul, which is incorporated into the NBLAST and XBLAST programs, available for public use through the website of the National Institutes of Health (U.S.A.). To obtain gapped alignments for comparison purposes, Gapped BLAST is utilized. When utilizing BLAST and Gapped BLAST programs, the default parameters of the respective programs (e.g., XBLAST and NBLAST) are used. "Percent homology" may be used in this document to describe fragments, variants or isoforms of amino acids sequences, but other ways of describing fragments, variants or isoforms may be employed alternatively to or in conjunction with homology.

The term "ligand" and the related terms used in the present disclosure refer to a compound or compounds that form a complex with PD-1 protein. The term "ligand" encompasses all compounds, regardless of their size or origin. For example, inorganic molecules, organic molecules, small molecules, biological molecules, non-biological molecules are all encompassed by the term "ligand."

The term "interaction" and the related terms refer to a type of physical or chemical interaction of one or more molecular subsets with itself (intramolecular) or other molecular subsets (intermolecular) or with components of an environment (environmental). Interaction types may be either enthalpic or entropic in nature and may reflect either nonbonded or bonded interactions. Examples of nonbonded interaction types include, but are not limited to, electrostatic interactions, van der Waals (or dispersion) interactions between time-varying dipole moments (often related to steric complementarity), short range repulsion between overlapping atomic orbitals, hydrogen bonding, interactions involved with metal ion coordination, or interactions with one or more ordered or structural waters. Other examples of nonbonded interaction types may also include one or more solvation effects such as electrostatic desolvation (including self-reaction field polarization effects, solvent screening in a dielectric medium or interactions with a solvent-based ionic atmosphere), the hydrophobic effect, cavitation energy, and surface tension. Examples of bonded interactions include, but are not limited to, the intramolecular strain associated with distortions of equilibrium bond lengths, angles, torsions, etc., or the energy gap between cis-trans modes or the energy differential associated with changes in chirality of one or more chiral center. Examples of entropic-based interactions include the loss of conformational entropy of molecular subsets (including loss of rotameric entropy for protein side chains) upon binding or the favorable entropy gain obtained by the release of one or more ordered waters. Other more exotic interaction types may include π-π stacking, charge transfer, or other quantum mechanical phenomena.

The term "hydrogen-bonding," "hydrogen bonds," and related terms relate to a partially electrostatic attraction between a hydrogen (H) which is bound to a more electronegative atom such as nitrogen (N) or oxygen (O) and another adjacent atom bearing a lone pair of electrons. For example, when it is stated that the nitrogen acts as a "hydrogen bond donor" it means that a hydrogen (H) bound to a nitrogen (N) is donated by the nitrogen as it electrostatically attracted to or accepted by an adjacent atom bearing a lone pair of electrons such as an oxygen. Similarly, when it is stated that an oxygen acts as a "hydrogen bond acceptor," it means that a hydrogen (H) bound to a more electronegative atom such as nitrogen (N) is electrostatically attracted to or "accepted by" an adjacent atom such as oxygen bearing a lone pair of electrons. Sometimes the hydrogen bonded atoms are called out without explicitly stating the origin and presence of an intermediate hydrogen atom. The term "hydrogen bonding" is used wherever LigPlot Plus software predicts a hydrogen bonding interaction using its algorithm and applied parameters of 3.35 Å for maximum distance between hydrogen bond donor and acceptor. Not all hydrogen bonds may actually be in place simultaneously; this is evident for atoms that are shown to form 4 putative hydrogen bonds, where however, at any given time only 3 hydrogen bonds are chemically possible. In general, although crystal structures such as the co-crystal structural information herein does not directly show or detect hydrogen bonding, the software used to describe the co-crystal does predict such H-bonding exists. Therefore, throughout the disclosure when a H-bond is present and described, it may be said to be "predicted" by software to be present.

The term "ionic bonding" and related terms include a type of chemical bond that involves the electrostatic attraction between oppositely charged ions, and is the primary interaction occurring in ionic compounds.

The term "van der Waals interaction" and related terms include weak, short-range electrostatic attractive forces between uncharged molecules, arising from the interaction of permanent or transient electric dipole moments.

The term "π-π interaction or π-π stacking" and related terms include attractive, noncovalent interactions between aromatic rings that are oriented either roughly parallel or roughly perpendicular (such as in "edge-face" interactions) to each other, since they contain π bonds.

The term "steric interactions," "steric effects" and the related terms describe molecular and/or atomic interactions that may arise in a number of ways. Steric effects are described, for example, in (48). For example, steric effects may result from repulsions between valence electrons or nonbonded atoms, leading to in an increase in the energy of the system. In the formation of a ligand-receptor complex, any group of atoms that is in van der Waals contact with the receptor or the biomolecule can be or is involved in the binding event. If a ligand binding pocket can adjust to any ligand, then no steric effect will be observed. If, however, the binding pocket has limited conformational flexibility, and this flexibility is not equivalent in all directions, then a steric effect will be observed. The steric effect will be dependent on conformational states, and the minimal steric interaction principle will probably be observed. This principle states that a substituent whose steric effect is conformationally variable will prefer a conformation that minimizes steric repulsions and will give rise to the smallest steric strain.

The term "binding site" and related terms refer to an area on the protein wherein a small molecule can interact with such as a region, which can be located on the surface or interior of the protein molecule. The term "pocket," "binding pocket" or related terms can refer to a cavity on the surface or in the interior of a protein molecule that possesses suitable properties for binding a ligand. Amino acid and other residues (such as co-factors) around a pocket determine its physicochemical characteristics. Residues outside the binding site can also have a long-range effect on the properties of the binding pocket. Binding pocket can have a concave surface presenting amino acid residues in a suitable configuration for binding low molecular weight compounds (which can be referred to as "small molecules"). The mobility of a protein molecule can permit opening, closing, and adaptation of binding pockets to regulate binding processes. The influence of protein flexibility on binding pockets can vary from small changes to an already existent pocket to the formation of a completely new pocket. Pockets and binding sites are described, for example, in (47).

Typically, a set of appropriate molecular descriptors describing each distinct configuration will be used to distinguish one configuration from another. Molecular descriptors may include, but are not limited to, a) chemical descriptors (e.g., element, atom type, chemical group, residue, bond type, hybridization state, ionization state, tautomeric state, chirality, stereochemistry, protonation, hydrogen bond donor or acceptor capacity, aromaticity, etc.); b) physical descriptors (e.g., charge, both formal and partial, mass, polarizability, ionization energy, characteristic size parameters, such as van der Waals [vdW] radii, vdW well depths, hydrophobicity, hydrogen bonding potential parameters, solubility, equilibrium bond parameters relating bond energies to bond geometries, etc.); c) geometrical descriptors (e.g., atomic coordinates, bond vectors, bond lengths, bond angles, bond torsions, suitable structural descriptors for rings, descriptors for molecular surfaces and volumes, such as solvent accessible surfaces and solvent-excluded volumes, etc.); and d) environmental descriptors (e.g., temperature, pH, ionic strength, pressure, etc.). Chemical descriptors may be assigned based on application of one or more rules or concepts of organic (or inorganic, if appropriate) chemistry to represent chemical structures that must at least stipulate basic structural information such as element type and bond connectivity (i.e., minimally which nonhydrogen atoms are connected to one another) but may also contain some form of coordinate information. Such chemical structures may be stored and received in a number of different data representations. One common example of data representation, though many others are also possible, is that of a PDB file. Examples of currently available software programs that can be used to assign chemical descriptors include SYBYL™ from Tripos, Chimera™ from UCSF, and WhatIf™ (for proteins), etc. Correct assignment of chemical descriptors may also include additional input regarding chiral centers and stereochemistry or even environmental factors, such as expected pH as related to assignment of ionization states.

The term "affinity formulation" and the related term refer to the energy model used to calculate approximate quantitative values for a given interaction type for a configuration associated with a molecular combination. Typically, there may be many different affinity formulations for a given interaction type from which to choose. The choice of affinity formulation may affect the amount of error associated with the quantitative approximation of a given interaction type. The choice of affinity formulation may also involve very different levels of modeling sophistication and hence computational complexity. A given affinity formulation may require one or more molecular descriptors for evaluation. Two different affinity formulations for a given interaction type may require a very different set of molecular descriptors, while others may share multiple molecular descriptors in common. For example, electrostatic interactions may be modeled according to an affinity formulation involving the use of a modified form of Coulomb's law with distance-dependent dielectric function as applied to a set of partial charges assigned to atomic centers in each molecular subset via use of a suitable force field. In another example, both electrostatic and electrostatic desolvation interactions may be modeled according to an affinity formulation involving a solution of the Poisson-Boltzmann equation (linear or nonlinear) along with an assumption of point charges embedded in solute spherical cavities with size defined by van der Waal radius of each atom and the solute spheres placed in a homogeneous dielectric medium representing water with and possibly containing an ionic atmosphere. Alternatively, electrostatic interactions may be modeled based on quantum-mechanical solution of electronic ground states for each molecular subset. In most scenarios the modified Coulomb with distance-dependent dielectric formulation will be cheaper to compute but less accurate than a Poisson-Boltzmann-based formulation let alone a full quantum-mechanical solution. As further examples, van der Waals interactions may be modeled according to an affinity formulation based on use of a generalized Lennard-Jones potential or alternatively based on a steric complementarity. Hydrogen-bonding interactions may be modeled according to an affinity formulation based on use of a 12-10 Lennard-Jones potential with an angular weighting function or by rescaling of partial charges and van der Waals radii of hydrogen bond donor and acceptor atoms such as that found in the Amber force field. The hydrophobic effect may be modeled according to an affinity formulation based on the fragmental volume approach or the solvent accessible surface area-based formalism. Intramolecular strain associated with dihedral changes may be modeled according to an affinity formulation based on use of Pitzer potentials or by inverse Gaussian torsional constraints. As yet another example, instead of using a Poisson Boltzmann-based formulation, electrostatic desolvation for a configuration may be modeled via an affinity formulation based on use of a variant of the Generalized Born approximation.

The term "computation strategy" herein refers to the computational technique used to quantitatively evaluate a given affinity formulation for one or more interaction types. The choice of computation strategy may be influenced by the available computational systems, apparatus, means and/or methods, the available memory capacity, and/or computing time constraints. As an example of different computational strategies for the same affinity formulation, consider the electrostatic interaction for target-ligand combination, for which a modified Coulombic affinity formulation with distance-dependent dielectric may be computed according to a computation strategy involving direct summation of pair-wise calculation between all possible pairs of partial charges across the protein and ligand. For a ligand with 100 atoms and a protein with 3000 atoms, this would entail the calculation of 300 K intermolecular distances let alone the number of distinct intramolecular pairs. An alternative computation strategy is to instead utilize a probe grid map approximation, whereby an electrostatic potential function associated with source charges on the protein is evaluated and stored on 3-D grid for coordinate locations enclosing the protein. Then for each ligand charge a corresponding electrostatic potential value is accessed from memory (or other storage) and the direct product of the charge and the potential is then accumulated over all charges in the ligand. This may significantly reduce computational effort especially in the context of screening a molecule library where many molecular combinations may feature the same target protein but different ligands. Of course, the probe grid map approximation may require significant storage in order to reduce numerical errors related to variation of the potential function. Moreover, such an approximation is only suitable when the source charges of the protein do not change positions between different configurations. An alternative for a target protein featuring a flexible binding pocket, may be to use a hybrid computation strategy involving the use of the pair-wise strategy for the portion of the protein containing mobile source charges and the probe grid map strategy for the remainder of the protein. In general, various different computation strategies may be applied to other affinity formulations for other interaction types. On the other hand, the choice of computation strategy may be limited by the nature of the affinity formulation or interaction type in question. For example, it is unlikely that one would a strategy appropriate for evaluation of intermolecular electrostatics interactions to instead compute intramolecular strain components involving bonded interactions. Other types of computational strategies exist than those based on pair-wise (e.g., interactions between pairs of atoms) or map or potential field (e.g., interactions of an atom with a potential field) calculations. For example, the evaluation of a Generalized Born solvation model based on the calculation of either volume integrals over the solvent excluded volume or on the calculation of surface integrals on the solvent accessible surface area. As yet another example, various formulations of bonded interactions may be evaluated according to a computation strategy featuring traversal of an appropriate data structure containing relevant coordinate and bond descriptors.

An "affinity function" is a composition of affinity components each of which corresponds to a combination of an interaction type, an affinity formulation, and a computation strategy. An affinity component may represent interactions for the whole or parts of one or more molecular subsets. An affinity function may contain multiple affinity components relating to the same interaction type. For example, two affinity components may represent the same interaction type but differ in either their affinity formulation and/or their computation strategy. Each distinct molecular configuration for a given molecular combination may produce different quantitative results for an affinity component and hence for the corresponding affinity function. In one embodiment, the analysis of a molecular combination may be based on determination of the configuration with the best value for the affinity function. In other embodiments, multiple favorable values for the affinity function corresponding to molecular configurations associated with one or more potential binding modes may be considered. In yet another embodiment, multiple affinity functions may be computed on one or more configurations of a molecular combination and some decision or action based on their joint consideration, such as for example the scenario of consensus scoring of a small finite number of configurations for each molecular combination explored in the course of screening a molecule library against a target molecule.

The terms "about" and "approximately" as used herein shall generally mean an acceptable degree of error for the quantity measured given the nature or precision of the measurements. Typical, exemplary degrees of error are within 20 percent (%); preferably, within 10%; and more preferably, within 5% of a given value or range of values. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written support for a claim limitation of, e.g., "0.98X." Alternatively, in biological systems, the terms "about" and "approximately" may mean values that are within an order of magnitude, preferably within 5-fold, and more preferably within 2-fold of a given value. Numerical quantities given herein are approximate unless stated otherwise, meaning that the term "about" or "approximately" can be inferred when not expressly stated. When "about" is applied to the beginning of a numerical range, it applies to both ends of the range.

As used herein, the terms "small molecule," "small organic molecule" and "small inorganic molecule" includes molecules (either organic, organometallic, or inorganic), organic molecules, and inorganic molecules, respectively, which have a molecular weight of more than about 50 Da and less than about 2500 Da. Small organic (for example) molecules may be less than about 2000 Da, between about 100 Da to about 1000 Da, or between about 100 Da to about 600 Da, or between about 200 Da to about 500 Da.

Drug Design and Discovery

Drug design and discovery processes (which can also be referred to as "drug development") can be divided into the following subprocesses: (1) target validation; (2) lead generation/optimization; (3) preclinical testing; and (4) clinical trials and approval. Target validation includes determination of one or more targets that have disease relevance. Results of the target validation phase might include a determination that the presence or action of the target molecule in an organism causes or influences some effect that initiates, exacerbates, or contributes to a disease for which a cure or treatment is sought. In some cases a natural binder or substrate for the target may also be determined via experimental methods. In the context of the present disclosure, a target is human PD-1 protein, with the examples of disease relevance being cancer start and/or progression, with or without treatment, some exemplary types of cancers being solid tumors and blood cancers, including metastatic cancer and cancers with high microsatellite instability and mismatch-repair deficient cancers. The types of cancers that may be relevant in the context of the present disclosure include, but are not limited to, colorectal cancer, gastrointestinal cancer, including stomach and esophageal cancer, endometrial cancer, breast cancer, prostate cancer, prostate cancer, bladder cancer, thyroid cancer, melanoma, lung cancer, head and neck cancer, including head and neck squamous cell carcinoma, or lymphoma, including Hodgkin lymphoma. Another examples of disease relevance are inherited disorders that lead to increased cancer predisposition, such as the syndromes that include mismatch repair deficiency and/or microsatellite instability, for example, Lynch syndrome.

Lead generation typically involves the identification of lead compounds, i.e., ligands, that can bind to the target molecule and that may alter the effects of the target through either activation, deactivation, catalysis, or inhibition of the function of the target, in which case the lead would be a viewed as a suitable candidate ligand to be used in the drug application process. In the context of the present disclosure, initial leads can be compounds that are identified in silico as being able to bind to a PD-L2 binding pocket of human PD-1 and determined to exert biological activity by in vitro and/or in vivo testing. Lead optimization involves the chemical and structural refinement of lead candidates into drug precursors in order to improve binding affinity to the desired target (human PD-1 in the context of the present disclosure), increase selectivity, and also to address basic issues of toxicity, solubility, and metabolism. Together lead generation and lead optimization can result in one or more chemically distinct leads for further consideration. In preclinical testing, biochemical assays and animal models are used to test the selected leads for various pharmacokinetic factors related to drug absorption, distribution, metabolism, excretion, toxicity, side effects, and required dosages. After the preclinical testing period, clinical trials and approval take place, during which the drug candidates are tested on human subjects for safety and efficacy.

A number of laboratory methods exist for measuring or estimating affinity between a target molecule and a ligand. Often the target might be first isolated and then mixed with the ligand in vitro and the molecular interaction assessed experimentally such as in the myriad biochemical and functional assays associated with high throughput screening. However, such methods are most useful where the target is simple to isolate, the ligand is simple to manufacture and the molecular interaction easily measured, but is more problematic when the target cannot be easily isolated, isolation interferes with the biological process or disease pathway, the ligand is difficult to synthesize in sufficient quantity, or where the particular target or ligand is not well characterized ahead of time. In the latter case, many thousands or millions of experiments might be needed for all possible combinations of the target and ligands, making the use of laboratory methods unfeasible.

While a number of attempts have been made to resolve this bottleneck by first using specialized knowledge of various chemical and biological properties of the target (or even related targets such as protein family members) and/or one or more already known natural binders or substrates to the target, to reduce the number of combinations required for lab processing, this is still impractical and too expensive in most cases. Instead of actually combining molecules in a laboratory setting and measuring experimental results, another approach is to use computers to simulate or characterize molecular interactions between two or more molecules (i.e., molecular combinations modeled in silico). The use of computational methods to assess molecular combinations and interactions is usually associated with one or more stages of rational drug design, whether structure-based, ligand-based, or both.

Computational Methods

Rational drug design can use structural information about drug targets (structure-based) and/or their natural ligands (ligand-based) as a basis for the design of effective lead candidate generation and optimization. In the context of the present disclosure, PD-L2 binding pocket of human PD-1 can serve as a drug target in the drug design process. In some cases, natural ligands PD-L1 and/or PD-L2 can serve as a basis for generating lead candidates. Structure-based rational drug design can utilize a three-dimensional model of the structure for the target. For target proteins or nucleic acids, such structures may be the result of X-ray crystallography/NMR or other measurement procedures or may result from homology modeling, analysis of protein motifs and conserved domains, and/or computational modeling of protein folding or the nucleic acid equivalent.

In the context of the present disclosure, the structure of the target can be a three-dimensional model of the PD-L2 binding pocket of human PD-1 that is computationally derived (generated) from the structures of the PD-L2 binding pocket of human PD-1 described in the present disclosure. For example, the three-dimensional model of the PD-L2 binding pocket of human PD-1 can be computationally derived from atomic coordinates, provided elsewhere in the present disclosure, corresponding to crystals of a variant of human PD-1 comprising amino acid substitutions, such as substitutions in one or more of the residues (for example, each of the residues) corresponding to N74, T76 or A132 of SEQ ID NO: 1. In some examples, in addition of a three-dimensional model of the PD-L2 binding pocket of human PD-1 that is computationally derived (generated) from the structures of the PD-L2 binding pocket of human PD-1 described in the present disclosure, structure-based in silico design, testing and/or optimization of human PD-1 ligands can also employ a three-dimensional model of human apo-PD-1 (meaning PD-1 without a ligand) that lacks a PD-2 binding pocket in a process that models formation of the PD-2 binding pocket and ligand-binding. The structure of a ligand may be computationally generated based on natural in vivo ligands, such as PD-1 and/or PD-2, or previously identified ligands. The ligand structure may instead be constructed ab initio from a known 2-D chemical representation using fundamental physics and chemistry principles, for example, when the ligand is not a biopolymer.

Rational drug design may incorporate the use of any of a number of computational components ranging from computational modeling of target-ligand molecular interactions and combinations to lead optimization to computational prediction of desired drug-like biological properties. The use of computational modeling in the context of rational drug design has been largely motivated by a desire both to reduce the required time and to improve the focus and efficiency of drug research and development, by avoiding often time consuming and costly efforts in biological "wet" lab testing and the like.

Computational modeling of target-ligand molecular combinations in the context of lead generation may involve the large-scale in silico screening of compound libraries, such as small-molecule libraries (i.e., library screening), whether the libraries are virtually generated and stored as one or more compound structural databases or constructed via combinatorial chemistry and organic synthesis, using computational methods to rank a selected subset of ligands based on computational prediction of bioactivity (or an equivalent measure) with respect to the intended target molecule.

In the context of the present disclosure, the target molecule is PD-1, and the structure of the target employed in the library screening can be a three-dimensional model of the PD-L2 binding pocket of human PD-1 that is computationally derived (generated) from the structures of the PD-L2 binding pocket of human PD-1 described in the present disclosure. For example, the three-dimensional model of the PD-L2 binding pocket of human PD-1 can be computationally derived from atomic coordinates, provided elsewhere in the present disclosure, corresponding to crystals of a variant of human PD-1 comprising amino acid substitutions, such as substitutions in one or more of the residues (for example, each of the residues) corresponding to N74, T76 or A132 of SEQ ID NO: 1. In some examples, in addition of a three-dimensional model of the PD-L2 binding pocket of human PD-1 that is computationally derived (generated) from the structures of the PD-L2 binding pocket of human PD-1 described in the present disclosure, computational library screening of human PD-1 ligands can also employ a three-dimensional model of human apo-PD-1 (meaning PD-1 without a ligand) that lacks a PD-2 binding pocket in a process that models formation of the PD-2 binding pocket and ligand-binding.

Fragment-based drug discovery (FBDD), discussed, for example, in (114) and (115), is another tool for discovering leads for drug development. FBDD first identifies starting points: low-molecular-weight ligands (~150 Da) (fragments) that bind to a target, for example, human PD-1. The fragments may bind to the target with the very low affinity. The identified fragments may be them grown or combined to produce leads with higher affinity. The three-dimensional binding mode of the fragments may be determined in silico and/or experimentally, using X-ray crystallography or NMR spectroscopy, and is used to facilitate their optimization into leads with higher activity. FBLD can be combined with screening.

Various terms and concepts are employed in computational modeling. For example, "binding mode" refers to the 3-D molecular structure of a potential molecular complex in a bound state at or near a minimum of the binding energy (i.e., maximum of the binding affinity), where the term "binding energy" (sometimes interchanged with "binding free energy" or with its conceptually antipodal counterpart "binding affinity") refers to the change in free energy of a molecular system upon formation of a potential molecular complex, i.e., the transition from an unbound to a (potential) bound state for the ligand and target. The term "system pose" is also sometimes used to refer to the binding mode. Here the term free energy generally refers to both enthalpic and entropic effects as the result of physical interactions between the constituent atoms and bonds of the molecules between themselves (i.e., both intermolecular and intramolecular interactions) and with their surrounding environment. Examples of the free energy are the Gibbs free energy encountered in the canonical or grand canonical ensembles of equilibrium statistical mechanics.

In general, the optimal binding free energy of a given target-ligand pair directly correlates to the likelihood of combination or formation of a potential molecular complex between the two molecules in chemical equilibrium, though, in truth, the binding free energy describes an ensemble of (putative) complexed structures and not one single binding mode. However, in computational modeling, it is usually assumed that the change in free energy is dominated by a single structure corresponding to a minimal energy. This is certainly true for tight binders (pK~0.1 to 10 nanomolar) but questionable for weak ones (pK~10 to 100 micromolar). The dominating structure is usually taken to be the binding mode. In some cases, it may be necessary to consider more than one alternative binding mode when the associated system states are nearly degenerate in terms of energy.

Binding affinity is of direct interest to drug discovery and rational drug design because the interaction of two molecules, such as a protein that is part of a biological process or pathway and a drug candidate sought for targeting a modification of the biological process or pathway, often helps indicate how well the drug candidate will serve its purpose. Furthermore, where the binding mode is determinable, the action of the drug on the target can be better understood. Such understanding may be useful when, for example, it is desirable to further modify one or more characteristics of the ligand so as to improve its potency (with respect to the target), binding specificity (with respect to other target biopolymers), or other chemical and metabolic properties.

When computationally modeling the nature and/or likelihood of a potential molecular combination for a given target-ligand pair, the actual computational prediction of binding mode and affinity is customarily accomplished in two parts: (a) "docking", in which the computational system attempts to predict the optimal binding mode for the ligand and the target and (b) "scoring", in which the computational system attempts to refine the estimate of the binding affinity associated with the computed binding mode. During library screening, scoring may also be used to predict a relative binding affinity for one ligand vs. another ligand with respect to the target molecule and thereby rank prioritize the ligands or assign a probability for binding.

Docking may involve a search or function optimization algorithm, whether deterministic or stochastic in nature, with the intent to find one or more system poses that have favorable affinity. Scoring may involve a more refined estimation of an affinity function, where the affinity is represented in terms of a combination of one or more empirical, molecular-mechanics-based, quantum mechanics-based, or knowledge-based expressions, i.e., a scoring function. Individuals scoring functions may themselves be combined to form a more robust consensus-scoring scheme using a variety of formulations. In practice, there are many different docking strategies and scoring schemes employed in the context of today's computational drug design.

Whatever the choice of computational method there are inherent trade-offs between the computational complexity of both the underlying molecular models and the intrinsic numerical algorithms, and the amount of computing resources (time, number of CPUs, number of simulations) that must be allocated to process each molecular combination. For example, while highly sophisticated molecular dynamics simulations (MD) of the two molecules surrounded by explicit water molecules and evolved over trillions of time steps may lead to higher accuracy in modeling the potential molecular combination, the resultant computational cost (i.e., time and computing power) is so enormous that such simulations are intractable for use with more than just a few molecular combinations. On the other hand, the use of more primitive models for representing molecular interactions, in conjunction with multiple, and often error-prone, modeling shortcuts and approximations, may result in more acceptable computational cost, but will decrease modeling accuracy and predictive power.

Methods and concepts related to computational aspects of drug discovery and drug design are described in the publications summarized below. The process of high throughput docking and scoring and its applications are discussed in (46) and (49). A general approach to the design, docking, and virtual screening of multiple combinatorial libraries against a family of proteins is described in (50). The use of multiple computers to accelerate virtual screening of a large ligand library against a specific target by assigning groups of ligands to specific computers is described in (51). A number of examples of software tools are used to perform docking simulations. These methods involve a wide range of computational techniques, including use of a) rigid-body pattern-matching algorithms, either based on surface correlations, use of geometric hashing, pose clustering, or graph pattern-matching; b) fragmental-based methods, including incremental construction or 'place and join' operators; c) stochastic optimization methods including use of Monte Carlo, simulated annealing, or genetic (or memetic) algorithms; d) molecular dynamics simulations or e) hybrids strategies derived thereof.

The earliest docking software tool was a graph-based rigid-body pattern-matching algorithm called DOCK, developed at UCSF back in 1982 (v1.0), with more recent versions including extensions to include incremental construction. Other examples of graph-based pattern-matching algorithms are described in include CLIX (which in turn uses GRID), FLOG and LIGIN. The above and other software tools are described in (52-56). Other rigid-body pattern-matching docking software tools are described in (57-60) and include the shape-based correlation methods of FTDOCK and HEX, the geometric hashing and the pose clustering. In general, rigid-body pattern-matching algorithms assume that both the target and ligand are rigid (i.e., not flexible) and hence may be appropriate for docking small, rigid molecules (or molecular fragments) to a simple protein with a well-defined, nearly rigid active site. Thus, this class of docking tools may be suitable for de novo ligand design, combinatorial library design, or straightforward rigid-body screening of a molecule library containing multiple conformers per ligand. Incremental construction based docking software tools include FlexX (61, 62) from Tripos (licensed from EMBL), Hammerhead (63), DOCK v4.0 (as an option), and the nongreedy, backtracking algorithm of (64). Programs using incremental construction in the context of de novo ligand design include LUDI (65) (from Accelrys) and GrowMol (66_. Docking software tools also include the tools based on 'place and join' strategies (67).

Incremental construction algorithms may be used to model docking of flexible ligands to a rigid target molecule with a well-characterized active site. They may be used when screening a library of flexible ligands against one or more targets. They are often comparatively less compute intensive, yet consequently less accurate, than many of their stochastic optimization based competitors. Incremental construction algorithms often employ one or more scoring functions to evaluate and rank different system poses encountered during computations. For example, FlexX was extended to FlexE (68) to attempt to account for partial flexibility of the target molecule's active site via use of user-defined ensembles of certain active site rotamers. Computational docking software tools based on stochastic optimization (69) are described in (70-72) and include ICM (from MolSoft), GLIDE (from Schrodinger), and LigandFit (from Accelrys), all based on modified Monte Carlo techniques, as well as AutoDock v.2.5 (from Scripps Institute) based on simulated annealing. Other software tools based on genetic or memetic algorithms are described in (73-76) and include GOLD, DARWIN, and AutoDock v.3.0 (also from Scripps).

Stochastic optimization-based methods may be used to model docking of flexible ligands to a target molecule. They generally use a molecular-mechanics-based formulation of the affinity function and employ various strategies to search for one or more favorable system energy minima. They are often more computer intensive, yet also more robust, than their incremental construction competitors. As they are stochastic in nature, different runs or simulations may often result in different predictions. Traditionally most docking software tools using stochastic optimization assume the target to be nearly rigid (i.e., hydrogen bond donor and acceptor groups in the active site may rotate), since otherwise the combinatorial complexity increases rapidly making the problem difficult to robustly solve in reasonable time.

Molecular dynamics simulations have also been used in the context of computational modeling of target-ligand combinations. This includes the implementations presented in (77) and (71) (along with Monte Carlo). In principle, molecular dynamics simulations may be able to model protein flexibility to an arbitrary degree. On the other hand, they may also require evaluation of many fine-grained, time steps and are thus often very time-consuming (one order of hours or even days per target-ligand combination). They also often require user interaction for selection of valid trajectories. Use of molecular dynamics simulations in lead discovery can be more suited to local minimization of predicted complexes featuring a small number of promising lead candidates. Hybrid methods may involve use of rigid-body pattern-matching techniques for fast screening of selected low-energy ligand conformations, followed by Monte Carlo torsional optimization of surviving poses, and finally even molecular dynamics refinement of a few choice ligand structures in combination with a (potentially) flexible protein active site. An example of this type of docking software strategy is (78).

There are a number of examples of scoring functions implemented in software and used to estimate target-ligand affinity, rank prioritize different ligands as per a library screen, or rank intermediate docking poses in order to predict binding modes. Scoring functions traditionally fall into three distinct categories: a) empirical scoring functions, b) molecular-mechanics-based expressions, or I knowledge-based scoring functions or hybrid schemes derived thereof. Empirically derived scoring functions (as applied to target-ligand combinations) were first inspired by the linear free-energy relationships often utilized in QSAR studies. An early example is that of Böhm et al. (65, 79) (used in LUDI). Other empirical scoring functions are described in (80-84) and include SCORE (used in FlexX), ChemScore, PLP, Fresno, and GlideScore v.2.0+ (modified form of ChemScore, used by GLIDE).

In general, empirical scoring functions comprise the bulk of scoring functions used today, especially in the context of large compound library screening. The basic premise is to calibrate a linear combination of empirical energy models, each multiplied by an associated numerical weight and each representing one of a set of interaction components represented in a (so-called) 'master scoring equation', where said equation attempts to well approximate the binding free energy of a molecular combination. The numerical weight factors may be obtained by fitting to experimental binding free energy data composed for a training set of target-ligand complexes. Molecular-mechanics-based scoring functions were first developed for use in molecular modeling in the context of molecular mechanics force fields like AMBER, OPLS, MMFF, and CHARMM (described in (85-89)). Examples of molecular-mechanics-based scoring functions include both the chemical and energy-based scoring functions of DOCK v.4.0 (based on AMBER), the objective functions used in GOLD, AutoDock v.3.0 (with empirical weights), and FLOG. In general, molecular-mechanics-based scoring functions may closely resemble the objective functions utilized by many stochastic optimization-based docking programs. Such functions typically require atomic (or chemical group) level parameterization of various attributes (e.g., charge, mass, van der Waals radii, bond equilibrium constants, etc.) based on one or more molecular mechanics force fields (e.g., AMBER, MMFF, OPLS, etc.). In some cases, the relevant parameters for the ligand may also be assigned based on usage of other molecular modeling software packages, e.g., ligand partial charges assigned via use of MOPAC (90), AMPAC (91) or AMSOL (92). They may also include intramolecular interactions (i.e., self-energy of molecules), as well as long range interactions such as electrostatics. In some cases, the combination of energy terms may again be accomplished via numerical weights optimized for reproduction of test ligand-target complexes.

Knowledge-based scoring functions were first inspired by the potential of mean force statistical mechanics methods for modeling liquids. Examples include DrugScore, PMF and BLEEP (93-95). In general, knowledge-based scoring functions do not require partitioning of the affinity function. However, they do require usage of a large database of 3-D structures of relevant molecular complexes. There is also usually no need for regression against a data set of molecular complexes with known experimental binding affinities. These methods are based on the underlying assumption that the more favorable an interaction is between two atoms, at a given distance, the more frequent its occurrence relative to expectations in a bulk, disordered medium. These schemes are sometimes referred to as 'inverse Boltzmann' schemes, but in fact the presence of local, optimized structures in macromolecules and protein folds means that distance-dependent pair-wise preference distributions need not be strictly Boltzmann. It is also possible to introduce the concept of singlet preferences based on other molecular descriptors, e.g., solvent accessible surface area for approximation of solvation effects. Hybrid scoring functions may be a mixture of one or more scoring functions of distinct type. One example is VALIDATE (96), which is a molecular-mechanics/empirical hybrid function. Other combinations of scoring functions may include the concept of consensus scoring in which multiple functions may be evaluated for each molecular combination and some form of 'consensus' decision is made based on a set of rules or statistical criteria, e.g., states that occur in the top 10% rank list of each scoring function (intersection-based), states that have a high mean rank (average-based), etc. A useful review discussion of consensus scoring can be found in (97). Various file formats exist for the digital representation of structural and chemical information for both target proteins and compounds as related to structural databases. Examples include the pdb, mol2 (from Tripos), and the SMILES formats.

A discussion on the calculation of total electrostatic energies involved in the formation of a potential molecular complex can be found in (98). Computational solutions of electrostatic potentials in the classical regime range from simpler formulations, like those involving distance-dependent dielectric functions, to more complex formulations, like those involving solution of the Poisson-Boltzmann equation (99, 100), a second order, generally nonlinear, elliptic partial differential equation. Other classical formalisms that attempt to model electrostatic desolvation include those based on the Generalized Born solvation model (101, 102), methods that involve representation of reaction field effects via additional solvent accessible or fragmental volume terms (103-105), or explicit representation of solvent in the context of molecular dynamics simulations (106-108). A lengthy review of full quantum mechanical treatment of electrostatics interactions can be found in (109).

Figure 6:
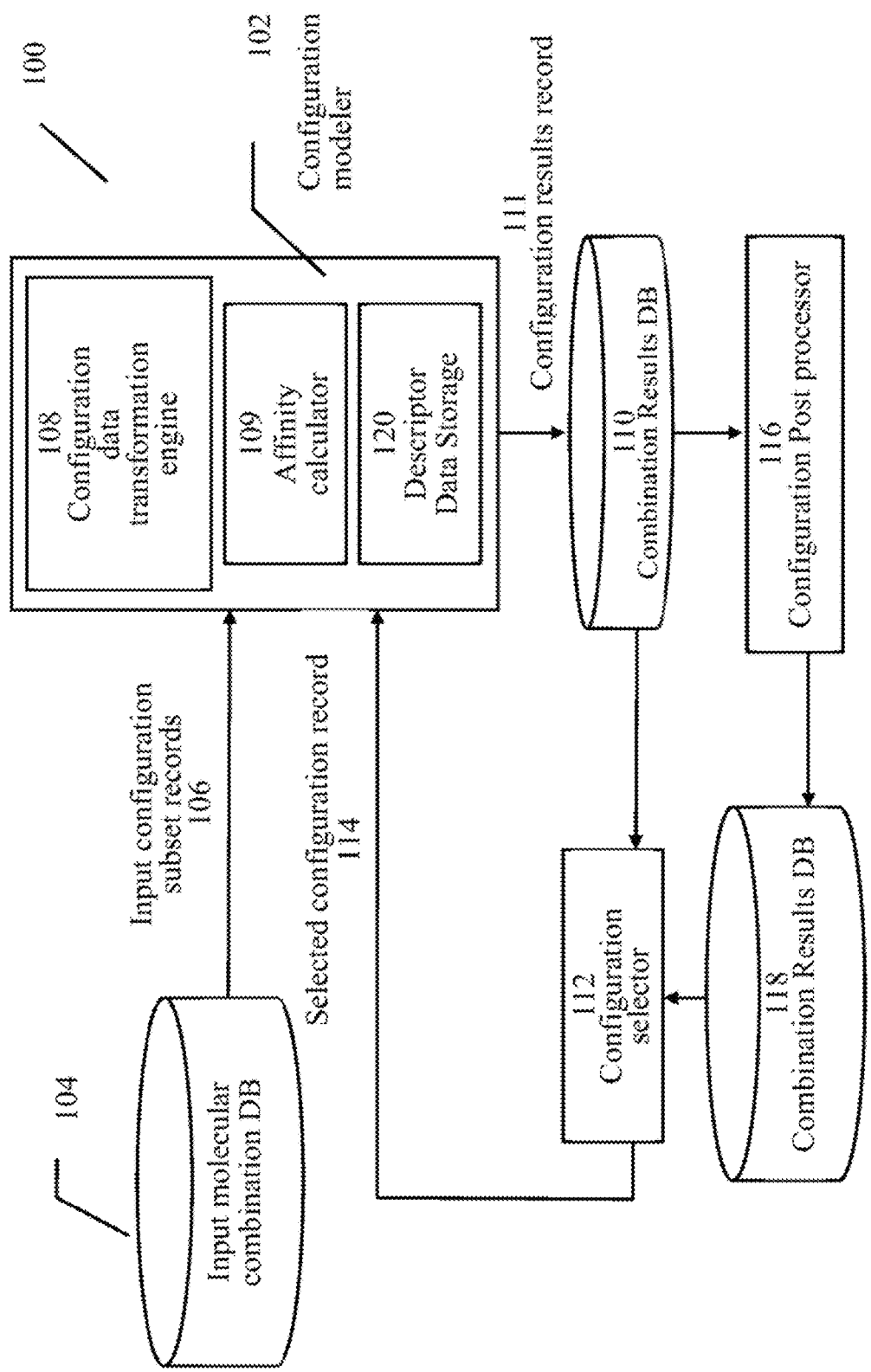
FIG. 6 is a schematic illustration of a system for performing exemplary methods according to the embodiments of the present invention.

FIG. 6 illustrates a modeling system 100 for the analysis of molecular combinations according to embodiments of the present disclosure. As shown, a configuration modeler 102 receives one or more input configuration records 106, including both the identities of and molecular descriptors for input structures for one or more molecular subsets from an input molecular combination database 104. The configuration modeler 102 comprises a configuration data transformation engine 108, an affinity calculator 109, and descriptor data storage 120. Results from the configuration modeler 102 are output as configuration results records 111 to a results database (DB) 110. Modeling system 100 may be used to determine or characterize one or more molecular combinations. In some embodiments, this may include, but is not limited to, prediction of likelihood of formation of a potential molecular complex, or a proxy thereof, the estimation of the binding affinity or binding energy between molecular subsets in an environment, the prediction of the binding mode (or even additional alternative modes) for the molecular combination, or the rank prioritization of a collection of molecular subsets (e.g., ligands) based on predicted bioactivity with a target molecular subset, and would therefore also include usage associated with computational target-ligand docking and scoring.

In a typical operation, many molecular combinations, each featuring many different molecular configurations, may be modeled. Since the total possible number of configurations may be enormous, the modeling system may sample a subset of configurations during the modeling procedure, though the sampling subset may still be very large (e.g., millions or billions of configurations per combination) and the selection strategy for configuration sampling is specified by one or more search and/or optimization techniques (e.g., steepest descent, conjugate gradient, modified Newton's methods, Monte Carlo, simulated annealing, genetic or memetic algorithms, brute force sampling, pattern matching, incremental construction, fragment place-and-join, etc.). An affinity function is evaluated for each visited configuration and the results for one or more configurations recorded in a storage medium.

The molecular combination may then be assessed by examination of the set of configuration results including the corresponding computed affinity function values. Once the cycle of computation is complete for one molecular combination, modeling of the next molecular combination may ensue. Alternatively, in some embodiments of the modeling system 100, multiple molecular combinations may be modeled in parallel as opposed to in sequence. Likewise, in some embodiments, during modeling of a molecular combination, more than one configuration may be processed in parallel as opposed to in sequence.

In one embodiment, modeling system 100 may be implemented on a dedicated microprocessor, ASIC, or FPGA. In another embodiment, modeling system 100 may be implemented on an electronic or system board featuring multiple microprocessors, ASICs, or FPGAs. In yet another embodiment, modeling system 100 may be implemented on or across multiple boards housed in one or more electronic devices. In yet another embodiment, modeling system 100 may be implemented across multiple devices containing one or more microprocessors, ASICs, or FPGAs on one or more electronic boards and the devices connected across a network.

In some embodiments, modeling system 100 may also include one or more storage media devices for the storage of various, required data elements used in or produced by the analysis. Alternatively, in some other embodiments, some or all of the storage media devices may be externally located but networked or otherwise connected to the modeling system 100. Examples of external storage media devices may include one or more database servers or file systems. In some embodiments involving implementations featuring one or more boards, the modeling system 100 may also include one or more software processing components in order to assist the computational process. Alternatively, in some other embodiments, some or all of the software processing components may be externally located but networked or otherwise connected to the modeling system 100.

In some embodiments, results records from database 110 may be further subjected to a configuration selector 112 during which one or more molecular configurations may be selected based on various selection criteria and then resubmitted to the configuration modeler 102 (possibly under different operational conditions) for further scrutiny (i.e., a feedback cycle). In such embodiments, the molecular configurations are transmitted as inputs to the configuration modeler 102 in the form of selected configuration records 114. In another embodiment, the configuration selector 112 may also send instructions to the configuration data transformation engine on how to construct one or more new configurations to be subsequently modeled by configuration modeler 102. For example, if the configuration modeler modeled ten target-ligand configurations for a given target-ligand pair (the target, in the context of the present disclosure, can be a PD-L2 binding pocket of human PD-1, and the ligand is a test ligand capable of interacting with the PD-L2 binding pocket of human PD-1), and two of the configurations had substantially higher estimated affinity than the other eight, then the configuration selector 112 may generate instructions for the configuration data transformation engine on how to construct further additional configurations (i.e., both target and ligand poses) that are structurally similar to the top two high-scoring configurations, which are then subsequently processed by the remainder of the configuration modeler 102. In some embodiments, the transmitted instructions may relate to construction from the resubmitted configurations whereas in other cases they relate to construction from the original input reference configuration(s).

In some embodiments, once analysis of a molecular combination is completed (i.e., all desired configurations assessed) a combination postprocessor 116 may be used to select one or more configuration results records from database 110 in order to generate one or more qualitative or quantitative measures for the combination, such as a combination score, a combination summary, a combination grade, etc., and the resultant combination measures are then stored in a combination results database 118. In one embodiment, the combination measure may reflect the configuration record stored in database 110 with the best observed affinity. In another embodiment, multiple high affinity configurations are submitted to the combination postprocessor 116 and a set of combination measures written to the combination results database 118. In another embodiment, the selection of multiple configurations for use by the combination postprocessor 116 may involve one or more thresholds or other decision-based criteria.

In a further embodiment, the selected configurations are also chosen based on criteria involving structural diversity or, alternatively, structural similarity (e.g., consideration of mutual rmsd of configurations, use of structure-based clustering or niching strategies, etc.). In yet another embodiment, the combination measures output to the combination results database 118 are based on various statistical analysis of a sampling of possibly a large number of configuration results records stored in database 110. In other embodiment the selection sampling itself may be based on statistical methods (e.g., principal component analysis, multidimensional clustering, multivariate regression, etc.) or on pattern-matching methods (e.g., neural networks, support vector machines, etc.)

In yet another embodiment, the combination results records stored in database 118 may not only include the relevant combination measures, but may also include some or all of the various configuration records selected by the combination postprocessor 116 in order to construct a given combination measure. For example, combination results records stored in database 118 may include representations of the predicted binding mode or of other alternative, high affinity (possibly structurally diverse) modes for the molecular combination. In another embodiment, the combination postprocessor 116 may be applied dynamically (i.e., on-the-fly) to the configuration results database 110 in conjunction with the analysis of the molecular combination as configuration results records become available. In yet another embodiment, the combination postprocessor 116 may be used to rank different configurations in order to store a sorted list of either all or a subset of the configurations stored in database 110 that are associated with the combination in question. In yet other embodiments, once the final combination results records, reflecting the complete analysis of the molecular combination by the configuration modeler 102, have been stored in database 118, some or all of the configuration records in database 110 may be removed or deleted in order to conserve storage in the context of a library screen involving possibly many different molecular combinations. Alternatively, some form of garbage collection or equivalent may be used in other embodiments to dynamically remove poor affinity configuration records from database 110.

In one embodiment, the molecular combination record database 104 may comprise one or more molecule records databases (e.g., flat file, relational, object oriented, etc.) or file systems and the configuration modeler 102 receives an input molecule record corresponding to an input structure for each molecular subset of the combination, and possibly a set of environmental descriptors for an associated environment. In another embodiment, when modeling target protein-ligand molecular combinations, the molecular combination record database 104 is replaced by an input target record database and an input ligand (or drug candidate) record database. In a further embodiment, the input target molecular records may be based on that are experimentally derived (e.g., X-ray crystallography, NMR, etc.), energy minimized, and/or model-built structures. In another embodiment, the input ligand molecular records may reflect energy minimized or randomized 3-D structures or other 3-D structures converted from a 2-D chemical representation, or even a sampling of low energy conformers of the ligand in isolation. In yet another embodiment, the input ligand molecular records may correspond to naturally existing compounds or even to virtually generated compounds, which may or may not be synthesizable.

In one embodiment the configuration data transformation engine 108 may transform one or more input molecular configurations into one or more other new configurations by application of various geometrical operators characterized by sets of geometrical descriptors. Transformation of molecular configurations into newer variants may be accomplished by one or more unary operations (i.e., acting on one input configuration, such as the mutation operator in a genetic algorithm), binary operations (i.e., acting on two input configurations, such as a binary crossover in a genetic algorithm), other n-ary operations (i.e., acting on a plurality of input configurations, such as a transform operator based on a population of configurations), or a combination thereof. In another embodiment, the transformation of molecular configurations into newer variants may result in multiple new configurations from one configuration, such as, for example, the construction of a suitable (often randomized) initial population for use in a genetic algorithm. In some embodiments, the configuration data transformation engine 108 may be able to construct ab initio one or more entirely new configurations without the requirement of input geometrical descriptors from an input molecular combination database 104, though other types of molecular descriptors may still be needed.

As already discussed, in some embodiments, the set of configurations generated via transformation during the course of an analysis of a molecular combination may be determined according to a schedule or sampling scheme specified by one or more search and/or optimization techniques used to drive the modeling processes of the configuration modeler 102. In some embodiments, the search strategy or optimization technique may be an iterative process whereby one or more configurations are generated from one or more input configurations, then affinities are calculated for each configuration, decisions are made based on affinity and/or structure, and all or part of the new set of configurations are used as input seeds for the next iteration; the process continuing until a specified number of iterations are completed configuration modeler 102 or some other convergence criteria satisfied. In such embodiments, the input configuration records 106 obtained or derived from data in the input molecular combination database 104, may serve only to initiate (or also possibly reset) the iterative process (i.e., prime the pump). For example, in the context of the present disclosure, the input target molecular records may be based on atomic coordinates of PD-L2 binding pocket of human PD-1 included in the present disclosure, which are determined from co-crystals of a variant of human PD-1 with PD-L2 ligand. In one example, the variant of human PD-1 is a variant comprising amino acid substitutions in one or more of (such as in each) of residues corresponding to N74, T76 or A132 of SEQ ID NO:1, In some embodiments, the search strategy or optimization technique may be stochastic in nature meaning that the set of configurations visited during analysis of a molecular combination may involve some random component and thus be possibly different between different runs of the configuration modeler 102 as applied to the same molecular combination. Here the term run refers to two different initiations of (possibly iterative) cycles of computation for analysis of the same molecular combination. In some embodiments, the combination postprocessor 116 may then base its results or decisions on configuration results records stored in database 110 but obtained from different runs. In some embodiments, the configuration data transformation engine 108 may produce new configurations sequentially, such as a new possible state associated with a given iteration of a Monte Carlo-based technique, and feed them to the affinity calculator 109 in a sequential manner. In other embodiments, the configuration data transformation engine 108 may produce multiple new configurations in parallel, such as a population associated with a given iteration of a genetic algorithm, and submit them in parallel to the affinity calculator 109. In other embodiments, the configuration data transformation engine 108 may not generate additional configurations and instead the configuration modeler 102 may operate solely on one or more input configuration records from the input molecular combination database 104, such as for example in some usages of modeling system 100 related to scoring of a set of known molecular configurations. In such embodiments, the configuration data modeler 102 may not include a search or optimization strategy and instead be used to perform affinity calculations on an enumerated set of input configuration records.

In some embodiments, various descriptor data related to the configurations of a given molecular combination may be stored or cached in one or more components of a descriptor data storage 120 via one or more storage (or memory) allocation means, structure or apparatus for efficient access and storage during the cycle of computations performed by the configuration modeler 102. In one embodiment, the descriptor data storage 120 may contain chemical or physical descriptors assigned to atoms, bonds, groups, residues, etc. in each of the molecular subsets or may even also contain environmental descriptors. In another embodiment, the descriptor data common to all configurations for a given molecular combination is compactly represented via a storage allocation means in one or more lookup tables. For example, often many physical and chemical descriptors may be identical for different configurations of a combination whereas one or more geometric descriptors are not.

In yet another embodiment, the descriptor data storage 120 may also contain relevant geometric descriptors for the configurations arranged in one or more storage formats via a prescribed storage allocation means. As examples, such formats may involve, but are not limited to, records analogous to pdb or mol2 file formats. Additional examples include various data structures such as those associated with the molecular representation partitioning shown in Ahuja I. As a further example, perhaps stored descriptors for atoms and bonds may represent individual nodes in one or more lists or arrays, or may alternatively be attached, respectively, to nodes and edges of a tree or directed graph.

The whole or parts of the input configuration records 106, and, if applicable, selected configuration records 114 chosen by configuration selector 112, may be converted to data representations used in the storage allocation means of the descriptor data storage 120. Data constructs contained in the descriptor data storage 120 may be either read (i.e., accessed) for use by the configuration data transformation engine 108 or the affinity calculator 109 and may be written either at the inception of or during the execution of a cycle of computation by the configuration modeler 102. The layout and access patterns for the associated descriptor data storage 120 will likely depend on the needs of the affinity calculator 109 as well as the configuration data transformation engine 108.

The affinity calculator 109 may comprise one or more processing (i.e., affinity) engines, where each affinity engine may be dedicated to performing calculations related to one or more affinity components as defined previously in regard to interaction types, affinity formulations, and computation strategies. In some embodiments, different affinity engines are assigned to each unique affinity component. In other embodiments, one or more affinity engines may compute multiple affinity components according to similarity of processing requirements. In yet other embodiments, different affinity engines may be grouped or otherwise arranged together to take advantage of common subsets of required input data in order to improve any caching scheme and/or to reduce the number of, the bandwidth requirements for, or the routing requirements for various associated data paths.

For example, in one embodiment, affinity components for both the electrostatic and van der Waals interactions involving field-based computation strategies utilizing stored pre-generated probe grid maps, may be computed on the same affinity engine, where said engine requires access to both types of probe grid maps in storage and to various numerical parameters used in evaluating the affinity formulation for the two different interactions. As another example, affinity components for both the hydrogen bonding and van der Waals interactions using affinity formulations featuring generalized Lennard-Jones potentials computed according to a pair-based computation strategy may be computed on the same affinity engine. In an alternative embodiment, the same two affinity components may be computed using two different affinity engines but grouped together in order to share common input data such as that relating to spatial coordinates and a subset of relevant chemical or physical descriptors.

In Vitro and In Vivo Methods

The methods related to drug design and discovery described in the present disclosure can include determining biological activity (including presence, absence or amount of biological activity, which can be also referred of "efficacy," of a candidate compound or molecule (which can be, but is not limited to, a small molecule) identified and/or designed by computational (in silico) methods in an in vitro biological assay or in vivo in a subject (such as a model animal, for example, a wild-type animal, a laboratory-bred animal, or a transgenic animal model). The methods disclosed in the present disclosure can also include validating or confirming in silico predicted activities of a ligand, for example, in silico binding of the ligand to PD-1 conformation of the target protein, with the results of an in vitro biological assay, and/or with the results of an in vivo study in an animal model.

One assay in vitro platform suitable for evaluation of the the ability of candidate compounds to block PD-1 interaction with its in vivo ligands is described in (116). The platform uses fluorescence-base transcriptional reporters based on the human Jurkat T cell line in conjunction with engineered T cell stimulator cell lines for investigating immune checkpoint signaling pathways, including PD-1 activity. A PD-1:PD-L2 cell-based inhibitor screening assay kit for conducting is a bioluminescent cell-based assay that can be used to screen and profile inhibitors of the PD-1:PD-L2 interaction is available from BPS Bioscience (San Diego, Calif.). In the above assay, as described in the assay data sheet, PD-1/NFAT Reporter/Jurkat T cells are used as effector cells; HEK293 cells over-expressing PD-L2 and an engineered T cell receptor (TCR) activator by transient transfection are used as target cells. When the cells are co-cultivated, TCR complexes on effector cells are activated by TCR activator on target cells, resulting in expression of the NFAT luciferase reporter. However, PD-1 and PD-L2 binding prevents TCR activation and suppresses the NFAT-responsive luciferase activity. In both scenarios, this inhibition can be specifically reversed by anti-PD-1 antibodies.

This interaction also can be blocked by anti-PD-L2 antibodies. These neutralizing antibodies block PD-1 signaling and promote T cell activation, resulting in reactivation of the NFAT-responsive luciferase reporter. Another example of an in vitro assay suitable for evaluation of the ability of candidate compounds to block PD-1 interaction with its ligand in vitro is competition ELISA described in (117). As described in (117), the assay measures the amount of biotin tagged PD-1 that is able to bind to the wells coated with PD-L1. Similarly, PD-L2 can be used as an in vivo ligand. An example of an in vitro assay for testing biological activity of candidate compounds, also described in (117), is an assay testing the ability of candidate compounds to promote T cell function. As described in (117), the production of IL-2 by peripheral blood mononuclear cells (PBMCs) pre-treated with PD-1/PD-L1 antagonists (or inhibitors): neutralizing mAbs or candidate compounds before stimulation with Staphylococcal enterotoxin B (SEB) for 72 hours. PBMCs include the cells that express/up-regulate both PD-1 (T cells) and PD-L1 (T cells, APCs) upon stimulation. In this assay, cytokine levels from cell culture supernatants would indicate that stimulated T cells treated with a-PD-1/PD-L1 antagonist produced significantly higher concentrations of IL-2 compared to untreated and stimulated cells, with the cells pre-treated by neutralizing mAbs serving as a positive control. Some other in vitro assays suitable for evaluating biological activity of candidate compounds are described in (118). In one assay, PBMC from normal healthy donors are seeded at $1\times10^5$ cells/well and stimulated with SEB in the presence of candidate compounds. IL-2 secretion by PMBC is measured by ELISA on day 3 after the stimulation. In another assay, mixed lymphocyte response is assessed by co-culturing $1\times10^5$ cells $CD4^+$ T cells with allogeneic monocyte-derived dendritic cells (DC) at a ratio of 10:1 (T:DC) in flat-bottom 96-well microtiter plates. $CD4^+$ T cells and DC are incubated for 6 days in the presence or absence of a candidate compound. Culture supernatants are harvested on day 5 for ELISA analysis of IFN-γ secretion. One more assay measures nonspecific T cell activation. In this assay, candidate compounds are mixed with samples of heparinized fresh human whole blood to measure cytokine release. After a 4-hour incubation at 37° C., the cells are pelleted, and the plasma fraction collected for measurement of IFN-γ, TNF-α, IL-2, IL-4, IL-6, and IL-10 using a cytokine cytometric bead array assay. Studies of potential anti-cancer effects of candidate compounds can also be performed in vitro in tumor-derived cell ilnes, such as D4m melanoma lines.

In vivo assays can be performed using animals, such as mice, with chemically induced or implanted tumors. Examples of in vivo assays using mouse models are described in (118). MC38 tumor cells are cultured in DMEM and implanted subcutaneously into female C57/B16 mice or B6.129S7-Ifngtm1Ts/J C57BL/6 mice. CT26 tumor cells are cultured in DMEM and implanted subcutaneously in female BALB/c mice. Tumor measurements are made 2-3 times weekly using an electronic caliper. Candidate compounds are administered to mice intraperitoneally on days 7, 10, and 13. For T-cell depletion studies, 500 µg of depleting antibodies for CD4 (GK1.5) or CD8 (53.6.72; BioXCell, W. Lebanon, N.H.) are administered on day 7. following subcutaneous implantation of MC38 tumor cells in the hind flank. The efficiency of $CD4^+$ or $CD8^+$ T cell depletion (>90%) is confirmed by FACS analysis of blood samples collected four days after administration of the depleting antibodies. Mice are sacrificed at the study termination or pre-determined endpoints. For immune response monitoring, tumors are harvested and processed using cell disruptors. The cell suspensions are clarified, pelleted, resuspended buffer or media, and counted. Cells are incubated with anti-CD16/32 mAb 24G.2 (BioXCell) to reduce background FcγR binding and then stained with antibodies specific for CD8, CD4, and CD45. Cells are also stained with the a fixable viability. For intracellular staining (ICS), cell samples are fixed, permeabilized, and stained with antibodies specific for FoxP3, Ki67, CTLA-4, IFN-γ, and TNF-α CT26 tumor antigen-specific $CD8^+$ T cells are identified using AH-1 MHC class I tetramers. Ex vivo AH-1 peptide stimulation is performed by culturing tumor or splenic cells with 2 µM AH-1 peptide (MBL) in the presence of brefeldin-A for 4 hours at 37° C. Ex vivo cytokine staining is performed by fixing and staining cells as described above, directly after tissue harvest. Samples are analyzed on FACS flow cytometers. Cytokine assays of harvested tumor cells can also be performed using bead-bays cytokine arrays. Immunohistochemical studies of tumor sections can also be performed according to established procedures.

Any of the methods described in the present disclosure can further comprise determining the toxicity of the ligand in an in vitro, in vivo or in silico assay. As used in the present disclosure, toxicity refers to a harmful effect on a cell or organism. For example, and not to be limiting, the cardiotoxicity or neurotoxicity of a compound can be determined. In vitro methods for assessing cardiotoxicity are known in the art. For example, electrophysiology measurements can be performed in cells, including, for example single cardiac cells. The effect of one or more compounds can be assessed in cell lines that express the human ether-a-go-go related gene (hERG1) or in cells transfected with hERG1. The hERG safety assay from Cyprotex (Watertown, Mass.) can also be used. Cardiotoxicity can also be measured in vivo by conducting an electrocardiogram (ECG) in a subject (e.g., a wild type animal or transgenic animal) expressing hERG1 after administering the compound to the animal. In vitro cytotoxicity panels can also be used to measure toxicity in individual cells. For example, assays that measure nuclear size, mitochondrial membrane potential, intracellular calcium, membrane permeability and/or cell number can be used. See, for example, the ADME-Tox panel available from EuroFins PanLabs, Inc. (Redmond, Wash.). In this assay, all five parameters are measured. Intracellular calcium and membrane permeability will increase in the presence of a cytotoxic compound. Conversely, nuclear size, cell number and mitochondrial membrane potential will decrease in the presence of a cytotoxic compound.

Genotoxicity studies can also be performed to identify mutagenic compounds. Gene mutations can be detected in bacteria, where they cause a change in growth requirements. The Ames test, which is conducted using *Salmonella typhimurium* is a widely used bacterial assay for the identification of compounds that can produce gene mutations, and it shows high predictive value with rodent carcinogenicity tests. Micronucleus assays can also be used to identify mutagenic compounds. Micronucleus formation is a hallmark of genotoxicity. Micronuclei are chromatin-containing bodies that represent fragments or even whole chromosomes that were not incorporated into a daughter cell nucleus at mitosis. The purpose of the assay is to detect those agents that induce chromosome damage leading to the induction of micronuclei in interphase cells. Assays that measure Cytochrome p450 (CYP) inhibition, CYP induction or drug transporter inhibition can also be performed.

Any of the methods provided in the present disclosure can further comprise determining if a candidate compound or molecule has an adverse drug reaction (ADR) or off-target effect in an in vitro, in vivo or in silico assay. It should be noted that off-target effects may be desirable or undesirable effects. In silico methods for determining off-target effects are known in the art. See, for example (110-112). In vitro assays for assessing off-target effects are also known in the art. See (113) for a review of in vitro assays that can identify undesirable off-target activity. Any of the methods provided herein can further comprise optimizing the ligand. A candidate compound or molecule can be modified or optimized for certain properties. For example, a candidate compound or molecule can be modified to reduce its toxicity, to reduce an undesirable off-target effect, to increase the binding affinity to a target protein, to decrease the binding affinity to a target protein, to increase a desirable off-target activity or to decrease an off-target activity.

Computer Systems

Any of the computer systems mentioned in the present disclosure may utilize any suitable number of subsystems. In some embodiments, a computer system includes a single computer apparatus, where the subsystems can be the components of the computer apparatus. In other embodiments, a computer system can include multiple computer apparatuses, each being a subsystem, with internal components. The subsystems can be interconnected via a system bus. Additional subsystems such as a printer, keyboard, storage device(s), monitor, which is coupled to display adapter, and others are shown. Peripherals and input/output (I/O) devices, which couple to I/O controller, can be connected to the computer system by any number of means known in the art, such as serial port. For example, serial port or external interface (e.g. Ethernet, Wi-Fi, etc.) can be used to connect computer system to a wide area network such as the Internet, a mouse input device, or a scanner. The interconnection via system bus allows the central processor to communicate with each subsystem and to control the execution of instructions from system memory or the storage device(s) (e.g., a fixed disk, such as a hard drive or optical disk), as well as the exchange of information between subsystems. The system memory and/or the storage device(s) may embody a computer readable medium. Any of the data mentioned herein can be output from one component to another component and can be output to the user.

A computer system can include a plurality of the same components or subsystems, e.g., connected together by external interface or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

The methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

EXAMPLES

The following examples are offered to illustrate, but not to limit the claimed invention.

Example 1: Materials and Methods

A. Yeast-Surface Display

Deep mutational scanning of the CC' and FG loops of human PD-1 was performed using a previously described PCR-based method (24). The PD-1 loop variant libraries were constructed using the *Saccharomyces cerevisiae* EBY100 strain. MACS and FACS experiments were performed using recombinant human PD-L2-Fc or PD-L-Fc proteins. The yeast strains and plasmids used in the study are summarized in Table 1.

TABLE 1

Plasmids and yeast strain.

| Yeast Strain (45) | Genotype |
|---|---|
| EBY100 | MATa AGA1::P$_{GAL1}$-AGA1::URA3 ura3-52 trp1 leu2Δ200 his3Δ200 pep4Δ::HIS3 prb1Δ1.6R can1 GAL |

| Plasmid | Description |
|---|---|
| pST892 | pRS414 P$_{GAL1}$-AGA2-PD-/(P21-E150) |
| pST992 | pRS414 P$_{GAL1}$-AGA2-PD-/(P21-E150) N74G |
| pST993 | pRS414 P$_{GAL1}$-AGA2-PD-1(P21-E150) T76P |
| pST995 | pRS414 P$_{GAL1}$-AGA2-PD-1(P21-E150) A132V |
| pST1013 | pRS414 P$_{GAL1}$-AGA2-PD-1(P21-E150) N74G T76P A132V |
| pST1132 | pET23d PD-1(N33-E150)-StrepII C93S N74G T76P A132V |
| pST1167 | pET23d PD-1(N33-E150)-StrepII C93S T76P A132V |
| pST971 | pADD2 PD-L1-Fc |
| pST972 | pADD2 PD-L2-Fc |
| pST980 | pADD2 Fc |
| pST981 | pADD2 PD-1-Fc |
| pST982 | pADD2 PD-1-Fc N74G |
| pST983 | pADD2 PD-1-Fc T76P |
| pST985 | pADD2 PD-1-Fc A132V |
| pST1008 | pADD2 PD-1-Fc N74G A132V |
| pST1009 | pADD2 PD-1-Fc T76P A132V |
| pST1010 | pADD2 PD-1-Fc N74G T76P A132V |
| pST739 | pADD2 PD-L1-His$_6$ |
| pST700 | pADD2 PD-L2-His$_6$ |
| pST963 | pADD2 PD-1-Fc C93S |
| pST964 | pADD2 PD-1-Fc C93S CC' loop-mutant (S71G P72G S73G N74G Q75G T76G D77G) |
| pST965 | pADD2 PD-1-Fc C93S FG loop-mutant (L128G A129G P130G K131G A132G Q133G) |
| pST966 | pADD2 PD-1-Fc C93S Pocket-mutant (Y68A I126A I134A E136A) |
| pST1195 | pADD2 PD-1(N33-E150)-Ctag C93S N74G T76P A132V N49S N58S N116D |
| pST1228 | pADD2 PD-1(N33-E150)-Ctag N49D N58D N74D N116D |
| pST1207 | pADD2 PD-L2(M1-Y123) N37D N64D |
| pST1249 | pADD2 PD-1-Fc V64E |
| pST1250 | pADD2 PD-1-Fc N66A |
| pST1251 | pADD2 PD-1-Fc Y68A |
| pST1252 | pADD2 PD-1-Fc Q75A |
| pST1253 | pADD2 PD-1-Fc I126D |
| pST1254 | pADD2 PD-1-Fc I134D |
| pST1255 | pADD2 PD-1-Fc E136A |
| pST1262 | pADD2 PD-L2-His$_6$ I103D |
| pST1263 | pADD2 PD-L2-His$_6$ I105D |
| pST1266 | pADD2 PD-L2-His$_6$ Y112A |
| pST1267 | pADD2 PD-L2-His$_6$ Y114A |

B. Bio-Layer Interferometry

BLI was performed on an Octet RED96® system at 30° C. in a buffer of 150 mM NaCl, 20 mM HEPES:NaOH pH 7.4, 0.1% BSA and 0.05% Tween 20. The human PD-1-Fc proteins were loaded onto anti-human IgG Fc capture (AHC) biosensors, associated in defined concentrations of human PD-L2-His6 or PD-L1-His6 proteins, and then dissociated in buffer.

TABLE 2

Crystallographic data collection and refinement statistics.

| | PD1$^{N74G\ T76P\ A132V}$/ PD-L2$^{IgV}$ | Apo- PD1$^{N74G\ T76P\ A132V}$ | Apo- PD1$^{T76P\ A132V}$ |
|---|---|---|---|
| Wavelength (Å) | 0.978 | 0.978 | 0.978 |
| Resolution range (Å) | 37.5-1.99 (2.06-1.99) | 36.5-1.18 (1.23-1.18) | 36.5-1.42 (1.48-1.42) |
| Space group | P 2121 21 | P 32 2 1 | P 32 2 1 |
| Unit cell | 41.3 67.8 89.7 90 90 90 | 46.2 46.2 89.3 90 90 120 | 46.2 46.2 89.4 90 90 120 |
| Total reflections | 185797 (11081) | 400313 (24984) | 171335 (11683) |
| Unique reflections | 17750 (1645) | 36661 (3544) | 21301 (2090) |
| Multiplicity | 10.4 (6.7) | 10.9 (7.0) | 8.0 (5.6) |
| Completeness (%) | 98.6 (90.6) | 99.7 (98.8) | 99.7 (98.2) |
| Mean I/sigma(I) | 16.1 (2.28) | 28.5 (2.79) | 23.3 (2.40) |
| Wilson B-factor | 35.8 | 16.7 | 21.9 |
| Rmerge | 0.139 (0.723) | 0.0521 (0.539) | 0.0903 (1.03) |
| CC$_{1/2}$ | 0.992 (0.780) | 0.999 (0.856) | 0.998 (0.769) |
| CC* | 0.998 (0.936) | 1.00 (0.960) | 0.999 (0.932) |
| R$_{work}$ | 0.196 (0.292) | 0.154 (0.192) | 0.158 (0.193) |
| R$_{free}$ | 0.226 (0.339) | 0.164 (0.233) | 0.189 (0.263) |
| Number of non-hydrogen atoms | 1782 | 1156 | 1143 |
| macromolecules | 1654 | 1001 | 1056 |
| water | 127 | 144 | 82 |
| Protein residues | 210 | 112 | 116 |
| RMS(bonds) (Å) | 0.013 | 0.009 | 0.016 |
| RMS(angles) (°) | 1.48 | 1.35 | 1.60 |
| Ramachandran favored (%) | 99 | 100 | 99 |
| Ramachandran outliers (%) | 0 | 0 | 0 |
| Clashscore | 8.32 | 0.99 | 5.66 |
| Average B-factor | 50.8 | 23.4 | 30.3 |
| macromolecules | 50.6 | 21.1 | 30.9 |
| solvent | 53.8 | 38.2 | 39.1 |

Statistics for the highest-resolution shell are shown in parentheses.

C. Protein Crystallization and X-Ray Crystallography

The human apo-PD-1N74G T76P A132V and human apo-PD-1T76P A132V proteins were over-expressed in and refolded from the inclusion bodies of *Escherichia coli* BL21(DE3) cells. The human apo-PD-1N74G T76P A132V protein was crystallized in 100 mM NaCl, 100 mM Tris:HCl pH 8.0, 27% (w/v) PEG-MME 5,000. The human apo-PD-1T76P A132V protein was crystallized in 100 mM NaCl, 100 mM Tris:HCl pH 8.0, 36% (w/v) PEG 3,350. The human PD-1N74G T76P A132V and human PD-L2IgV protein complex was produced using the human Expi293F cell line. The complex was crystallized in 200 mM magnesium acetate, 10% (w/v) PEG 8000. All X-ray diffraction data were collected at the SSRL beam lines 12-2 or 14-1, and processed using HKL-3000 (42). Molecular replacement, refinement and density modification were performed in Phenix (43) and model building in Coot (44). The crystallographic data collection and refinement statistics are summarized in Table 2.

Example 2: Engineering Human PD-1 Loop Variants with Enhanced PD-L2 Affinity Substantial earlier efforts (23) to crystalize the human PD-1/PD-L2 complex were unsuccessful. Previous studies (16, 17, 19) indicated that the PD-1 ligand-binding interface comprises a hydrophobic core, the CC' loop and the FG loop, and that formation of a complex with ligands results in loop movement and pocket formation in the hydrophobic core. In the present study, it was conceived that mutations in these two loops of PD-1 were coupled to pocket formation and may alter the affinity for PD-L2. It was then experimentally confirmed that poly-glycine mutants of these loops in human PD-1 significantly decreased its affinities for PD-L2 (data not shown). The binding of sensor-loaded PD-1, the glycine-loop-mutants and the pocket mutant to 1.9 µM PD-L2 (left) and 17 μM PD-L1 (right) was measured using biolayer interferometry. Corresponding PD-1-Fc proteins were loaded onto anti-human IgG Fc capture (AHC) biosensors. Association was monitored for 2 min and dissociation for 2 min. Since the present study was particularly interested in the structure of the PD-1 pocket when bound to PD-L2, the residues in the hydrophobic core were maintained, and directed evolution was performed exclusively in the CC' loop (residues 70-78) and the FG loop (residues 127-133) of human PD-1. Deep mutational scanning (24, 27) was used to construct loop-variant libraries with trinucleotides encoding each of 20 residues at each position. Next, yeast-surface display (25) was used with a recombinant human PD-L2-human Fc fusion protein as the selection agent. After two rounds of selection using magnetic- and fluorescent-activated cell sorting (MACS and FACS), human PD-1 loop-variant clones with single-residue substitutions were isolated (data not shown). Substitutions at two residues were identified in the CC' loop (N74G and T76P), and at one residue in the FG loop (A132V, A132L). In contrast, when the same yeast library was used for section with PD-L1-Fc, only the A132 substitutions were isolated as high-affinity variants (data not shown). This result suggested that the N74G and T76P variants were PD-L2-binding specific. $PD\text{-}1^{T76}$ was chosen as a template to generate a second PD-1 loop variant library and selected for further enhancement of PD-L2 binding. As a result, a PD-1 triple mutant was obtained, which contained all three substitutions identified from the first library, N74G, T76P and A132V.

Example 3: PD-1 Loop Variants Showed Increased Binding Affinity and Association Kinetics for PD-L2 and PD-L1

To validate the enhanced affinity of PD-1 loop variants, human PD-1 and the loop variants, as well as human PD-L2 and PD-L1 ectodomain proteins, were recombinantly expressed and purified. Using bio-layer interferometry (BLI), the binding of PD-L2 to wild-type PD-1 and the variants was compared (data not shown). The binding of sensor-loaded PD-1 and the loop variants to 190 nM PD-L2 and 1.1 μM PD-L1 was measured using biolayer interferometry. Corresponding PD-1-Fc proteins were loaded on anti-human IgG Fc capture (AHC) biosensors. Association was monitored for 2 min and dissociation for 2 min. Fitting of binding curves was performed in Graphpad Prism 8 software using built-in equations of "Receptor binding—kinetics" models. Means and standard deviations were calculated from 3-4 independent experiments. Wild-type PD-1 bound PD-L2 with a $K_D$ of 500 nM. The variants all exhibited increased PD-L2 affinity, with $K_D$ of 170 nM for N74G, 12 nM for T76P, and 69 nM for A132V. Remarkably, the PD-1 triple mutant had a $K_D$ of 2.6 nM, exhibiting a ~200-fold increase in PD-L2 binding affinity. Table 3 summarizes the binding affinity ($K_D$) and kinetic parameters (association constant $k_{on}$, dissociation constant $k_{off}$) for the PD-1 loop variants binding to PD-L2 or PD-L1. Fitting of binding curves was performed in Graphpad Prism 8 using built-in equations of "Receptor binding—kinetics" models. Means and standard deviations were calculated from 3-4 independent experiments. The triple-mutant also showed substantially increased affinity for PD-L1. The A132V mutant showed increased affinity for PD-L1, consistent with previous reports (19, 23, 28, 29), but the N74G and T76P single mutants had minor effects. Thus, a human PD-1 triple-mutant exhibited potent binding affinity enhancement for both PD-L1 and PD-L2. Kinetic measurements of binding of the ligands by PD-1 with BLI also permitted the determination of association constants ($k_{on}$). Compared to wild-type PD-1, all loop variants showed increased k, for binding PD-L2. The PD-1 triple mutant showed a 3-fold increase of $k_{on}$ for PD-L2, and 14-fold for PD-L1. These results suggested that these amino acid substitutions in the loops stabilized the ligand-bound state among the conformational ensembles of apo-PD-1 (17, 19).

TABLE 3

Binding affinity ($K_D$) and kinetic parameters (association constant $k_{on}$, dissociation constant $k_{off}$) for the PD-1 loop variants binding to PD-L2 or PD-L1.

| | Binding hPD-L2 | | | Binding hPD-L1 | | |
|---|---|---|---|---|---|---|
| hPD-1 | $K_D$ (nM) | $k_{on}$ ($10^5$/M · s) | $k_{off}$ ($10^{-2}$/s) | $K_D$ (nM) | $k_{on}$ ($10^5$/M · s) | $k_{off}$ ($10^{-2}$/s) |
| Wild-Type | 500 ± 82 | 1.8 ± 0.44 | 8.4 ± 0.50 | 4,100 ± 110 | 0.36 ± 0.025 | 15 ± 1.4 |
| N74G | 170 ± 24 | 2.9 ± 0.39 | 4.7 ± 0.07 | 20,000 ± 430 | 0.097 ± 0.026 | 17 ± 3.0 |
| T76P | 12 ± 5.4 | 5.0 ± 0.96 | 0.56 ± 0.11 | 2,700 ± 290 | 0.42 ± 0.024 | 11 ± 1.3 |
| A132V | 69 ± 9.6 | 4.8 ± 0.76 | 3.3 ± 0.47 | 90 ± 23 | 5.3 ± 0.52 | 4.7 ± 0.73 |
| N74G T76P A132V | 2.6 ± 0.62 | 5.8 ± 0.74 | 0.14 ± 0.01 | 72 ± 20 | 5.2 ± 0.80 | 3.6 ± 0.41 |
| N74G T76P | 92 ± 1.3 | 3.5 ± 0.25 | 0.32 ± 0.03 | 2,700 ± 130 | 0.33 ± 0.020 | 89 ± 0.080 |
| N74G A132V | 22 ± 4.9 | 4.5 ± 0.41 | 0.96 ± 0.12 | 94 ± 23 | 5.2 ± 0.85 | 4.7 ± 0.35 |
| T76P A132V | 2.6 ± 0.29 | 5.5 ± 0.18 | 0.14 ± 0.010 | 82 ± 18 | 4.8 ± 0.69 | 3.9 ± 0.28 |

Example 4: X-Ray Crystal Structure of the Human PD-1/PD-L2 Complex

The human PD-1/PD-L2 complex was crystallized using the PD-1 triple mutant. Site-directed mutagenesis was used to remove all N-linked glycosylation sites in each protein in an effort to aid crystallization, as illustrated by the protein sequences summarized in Table 4. Co-expression of the PD-1 triple mutant and the PD-L2 IgV domain yielded a stable and 1:1 stoichiometric complex, which was purified. The crystals of the human PD-1$^{N74G\ T76P\ A132V}$/PD-L2$^{IgV}$ complex were successfully obtained, and a 2.0 Å resolution structure of the complex by X-ray crystallography was determined. The structure is illustrated, for example, in FIG. 1A. The crystal contained one PD-1/PD-L2 complex per asymmetric unit, with space group P 2$_1$ 2$_1$ 2$_1$. The crystallographic data collection and refinement statistics are summarized in Table 2. The human PD-1/PD-L2 complex adopted an architecture similar to the previously determined murine PD-1/PD-L2 complex (19) with a Cα root-mean-square deviation (R.M.S.D.) of 3.8 Å.

TABLE 4

Amino acid sequences.

| Amino acid sequence | Plasmid (Parent) |
|---|---|
| >PD-1_N74G_T76P_A132V<br>MNPPTFSPALLVVTEGDNATFTCSFSNTSE<br>SFVLNWYRMSPSGQPDKLAAFPEDRSQPGQ<br>DSRFRVTQLPNGRDFHMSVVRARRNDSGTY<br>LCGAISLAPKVQIKESLRAELRVTERRAE<br>_GS_WSHPQFEK (SEQ ID NO: 2) | pST1132 (pET23d) |
| >PD-1_T76P_A132V<br>MNPPTFSPALLVVTEGDNATFTCSFSNTSE<br>SFVLNWYRMSPSNQPDKLAAFPEDRSQPGQ<br>DSRFRVTQLPNGRDFHMSVVRARRNDSGTY<br>LCGAISLAPKVQIKESLRAELRVTERRAE<br>_GS_WSHPQFEK (SEQ ID NO: 3)<br><br>_Linker_, Strep-tag ®II | pST1167 (pET23d) |
| >PD-1_N74G_T76P_A132V<br>_MGWSCIILFLVATATGVHS_NPPTFSPALLV<br>VTEGDSATFTCSFSSTSESFVLNWYRMSPS<br>GQPDKLAAFPEDRSQPGQDSRFRVTQLPNG<br>RDFHMSVVRARRDDSGTYLCGAISLAPKVQ<br>IKESLRAELRVTERRA_EPEA_<br>(SEQ ID NO: 4) | pST1195 (pADD2) |
| >PD-L2_IgV<br>_MIFLLLMLSLELQLHQ_IAALFTVTVPKELY<br>IIEHGSDVTLECNFDTGSHVNLGAITASLQ<br>KVEDDTSPHRERATLLEEQLPLGKASFHIP<br>QVQVRDEGQYQCIIIYGVAWDYKYLTLKVK<br>ASY (SEQ ID NO: 5)<br><br>Signal sequence, C-tag | pST1207 (pADD2) |

Figure 4B:
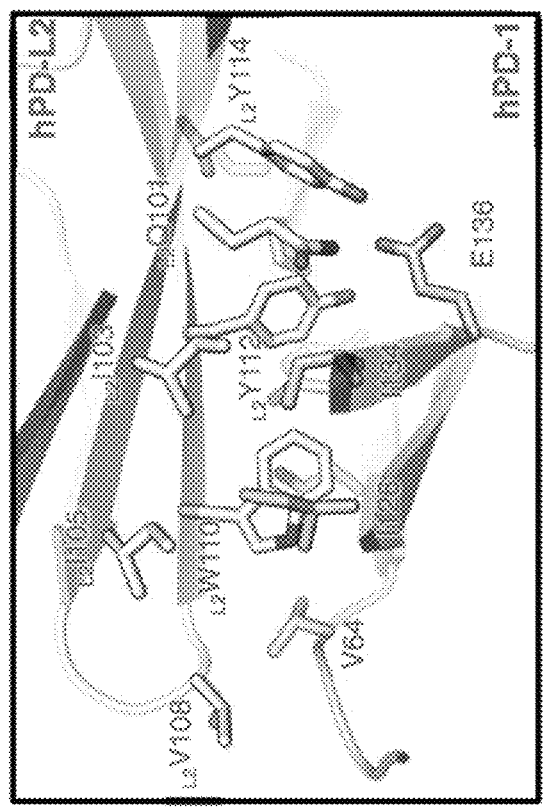
FIGS. 4A and 4B show ribbon diagrams schematically illustrating human PD-1/PD-L2 binding interface.
Figure 4A:
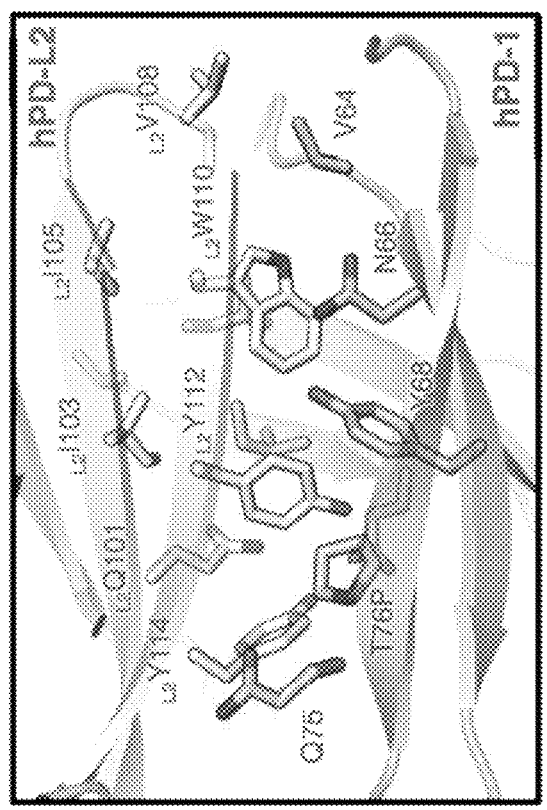
Figure 5A:
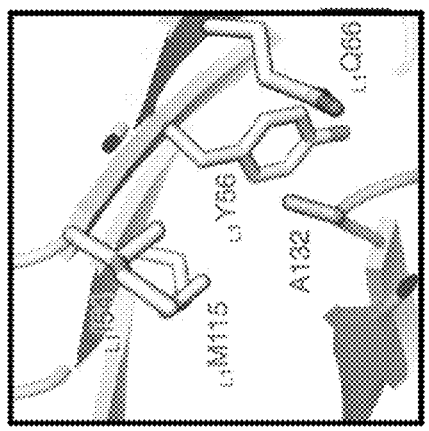
FIGS. 5A, 5B, 5C and 5D show ribbon diagrams schematically illustrating human PD-1/PD-L2 binding interface.
Figure 5B:
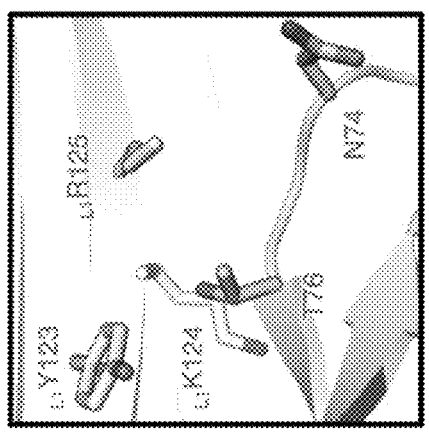
Figure 5C:
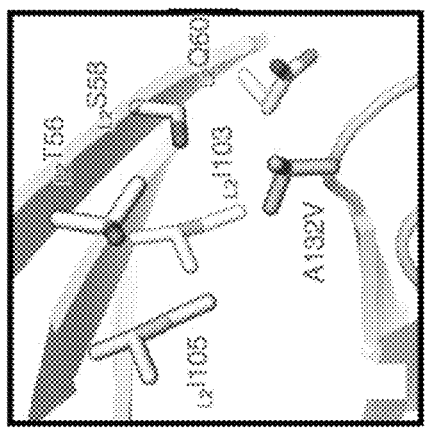
Figure 5D:
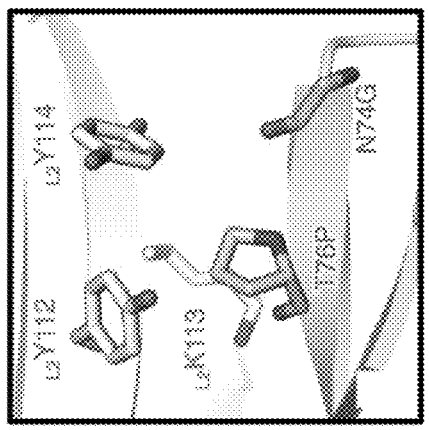

The structure of human PD-1/PD-L2 complex revealed that human PD-1/PD-L2 interface was formed by the front β-sheets of both IgV domains, as illustrated in FIG. 1B, burying 1,840 Å$^2$ (14% of the total) of solvent-accessible surface area. In the interface, notable interacting residues included the three highly conserved aromatics W110$_{L2}$, Y112$_{L2}$ and Y114$_{L2}$ from 3G of the PD-L2 IgV domain. The sidechains of these residues pointed into the center of the PD-1 ligand-binding surface, as illustrated in FIGS. 4A and 4B. To validate the interactions observed at the PD-1/PD-L2 interface, site-directed mutagenesis on several PD-1 and PD-L2 interfacial residues was performed. Using BLI, reduced binding of PD-1 interface mutants to PD-L2, and PD-L2 interface mutants to PD-1 was observed. The observed reduced binding was consistent with the structure of human PD-1/PD-L2 complex. The high-affinity loop substitutions of PD-1 localized to the interface, as illustrated in FIG. 1B. Among them, T76P and A132V made additional contacts to PD-L2, likely contributing to the increase in affinity, as illustrated in FIG. 5.

Example 5: X-Ray Crystal Structures of Human Apo-PD-1 Loop Variants

To assist analyses of the conformational change of PD-1 associated with PD-L2 binding, two human apo-PD-1 loop variants (see Table 4 for the amino acid sequences) were crystallized and their X-ray crystal structures were determined at 1.2 Å and 1.4 Å resolution, for PD-1$^{N74G\ T76P\ A132V}$ and PD-1$^{T76P\ A132V}$, respectively. Crystals of both variants contain a single PD-1 molecule per asymmetric unit, with space group P 3$_2$ 2 1 (see Table 2 for crystallographic data collection and refinement statistics). Both PD-1 variants were well-defined by the electron density maps with a notable exception of the CC' loop discussed further below. Superimposing the apo and PD-L2-bound PD-1$^{N74G\ T76P\ A132V}$ structures resulted in a Cα R.M.S.D. of 1.6 Å. The C'D loop of PD-1 (residues 83-92) was previously known to be a major part of the pembrolizumab epitope (30-32). This loop was not previously resolved in structures of human PD-1 without pembrolizumab (17, 23, 33), but it was clearly in both apo-PD-1 structures described in the present disclosure. The results of the structure determination indicated that the conformation of the loop changed significantly upon antibody binding.

Example 6: Formation of a Prominent Pocket in Human PD-1 Upon Binding PD-L2, with Human PD-1 Pocket Having Architecture Distinct from that of Murine PD-1 Pocket The structures of the human PD-1/PD-L2 complex and apo-PD-1 variants described in the present disclosure permitted the examination of formation of human PD-1 pocket in the PD-1/PD-L2 interface. Although human apo-PD-1 has a flat ligand-binding interface, as illustrated in FIG. 2A, the structures described in the present disclosure revealed that there were rearrangements in this interface upon binding of PD-L2. These rearrangements involved residues in βC (F63, V64, N66, Y68), 3F (L122, G124, I126), 3G (I134, E136) and the C'D loop (E84) forming a deep and extended pocket (illustrated in FIG. 2B), accommodating PD-L2 sidechains including the aromatic residues W110$_{L2}$ and Y112$_{L2}$, as illustrated in FIG. 2C. Each of these residues in PD-1 is within 4.4 Å of a PD-L2 residue (Table 5).

TABLE 5

A list of atoms from PD-L2 residues within 6.0 Å distance of the PD-1 pocket residues shown in FIG. 2B. Distance measurements were generated by COCOMAPS.

| | PD-1 | | | PD-L2 | | | Distance |
|---|---|---|---|---|---|---|---|
| | Residue | Number | Atom | Residue | Number | Atom | (Å) |
| βC | Phe | 63 | CB | Trp | 110 | NE1 | 4.7 |
| | Phe | 63 | CE1 | Ile | 105 | CG2 | 4.2 |
| | Phe | 63 | CD1 | Val | 108 | O | 4.0 |
| | Phe | 63 | CE1 | Gly | 107 | O | 4.2 |
| | Val | 64 | CG2 | Ala | 109 | N | 4.1 |
| | Val | 64 | CG2 | Val | 108 | O | 3.0 |
| | Val | 64 | O | Trp | 110 | NE1 | 3.0 |
| | Asn | 66 | ND2 | Asp | 111 | CA | 4.4 |
| | Asn | 66 | ND2 | Trp | 110 | O | 2.9 |
| | Tyr | 68 | CE1 | Lys | 113 | NZ | 5.3 |
| | Tyr | 68 | OH | Trp | 110 | CZ3 | 3.5 |

TABLE 5-continued

A list of atoms from PD-L2 residues within 6.0 Å distance of the PD-1 pocket residues shown in FIG. 2B. Distance measurements were generated by COCOMAPS.

| | PD-1 | | | PD-L2 | | | Distance |
|---|---|---|---|---|---|---|---|
| | Residue | Number | Atom | Residue | Number | Atom | (Å) |
| C'D | Glu | 84 | E1 | Ala | 109 | CB | 3.4 |
| loop | Glu | 84 | OE2 | Phe | 21 | N | 3.0 |
| | Glu | 84 | OE2 | Thr | 22 | N | 6.0 |
| | Glu | 84 | OE1 | Trp | 110 | N | 4.6 |
| | Glu | 84 | OE2 | Leu | 20 | CD2 | 3.2 |
| | Glu | 84 | OE1 | Val | 108 | O | 5.5 |
| βF | Leu | 122 | CD1 | Tyr | 112 | OH | 4.3 |
| | Ile | 126 | CG2 | Val | 108 | O | 5.7 |
| | Ile | 126 | CD1 | Ile | 104 | O | 5.8 |
| | Ile | 126 | CD1 | Ile | 103 | CG2 | 3.8 |
| | Ile | 126 | CG2 | Trp | 110 | NE1 | 3.5 |
| | Ile | 126 | CD1 | Ile | 105 | CD1 | 3.5 |
| βG | Ile | 134 | CB | Gln | 101 | NE2 | 4.0 |
| | Ile | 134 | CG1 | Tyr | 112 | CG | 3.9 |
| | Ile | 134 | CG1 | Ile | 103 | CD1 | 3.7 |
| | Ile | 134 | CD1 | Trp | 110 | CZ3 | 3.4 |
| | Ile | 134 | CD1 | Asp | 111 | O | 5.6 |
| | Glu | 136 | OE2 | Tyr | 114 | OH | 2.6 |
| | Glu | 136 | OE2 | Gln | 101 | NE2 | 4.4 |
| | Glu | 136 | OE2 | Tyr | 112 | OH | 2.6 |

Comparison of the PD-1 pockets in the human and murine PD-1/PD-L2 complexes demonstrated striking differences in pocket geometries. Human PD-1 pocket adopted an open, funnel-shaped architecture. Compared to murine PD-1 pocket, human PD-1 pocket has a wider entrance and a narrower exit (illustrated in FIG. 2B). The structured described in the present disclosure revealed that distinct pocket geometries arise from at least two considerations. First, human PD-1 was revealed to employ a different subset of interfacial residues to form the pocket, as compared to murine PD-1. Human PD-1 lacks an ordered βC'' strand, and thus the open pocket in human PD-1 is formed by rearranging residues F63, V64 and E84. In contrast, murine PD-1 pocket is closed with sidechains of A81 and S83 forming a boundary. Second, several sequence variations exist among the residues that form the pocket. For example, V64 and Y68 in human PD-1 are substituted with M64 and N68 in murine PD-1, respectively. To quantitatively evaluate the pocket dimensions, pocket volumes were measured using POCASA 1.1 (34). Human and murine PD-1 pockets were measured to have volumes of 130 Å$^3$ and 154 Å$^3$, respectively. Notably, these pockets were comparable in size to other protein cavities with established small-molecule inhibitors (20, 21, 35).

The structure of human PD-1/PD-L2 described in the present disclosure was compared with the previously determined human PD-1/PD-L1 structure (17). Superimposing the two structures resulted in a Ca R.M.S.D. of 1.5 Å for PD-1 residues. Binding PD-L1 triggered formation a much smaller cavity in human PD-1, as compared to binding of PD-L2, with the cavity having a measured volume of 40 Å$^3$. PD-L1 lacks a large aromatic sidechain corresponding to W110$_{L2}$, so the PD-1 rearrangement was revealed to involve only a small subset of the interfacial residues to accommodate the sidechain of Y123$_{L1}$, corresponding to PD-L2 residue Y112$_{L2}$. These results showed that the core of the human PD-1 interface had remarkable structural plasticity and the ability to form pockets with varied dimensions, permitting the interactions with different PD-1 ligands.

Example 7: The CC' Loop in the Triple-Mutant PD-1 Adopts a Ligand-Bound Conformation in the Absence of Ligand Conformational changes in the CC' and FG loops upon binding of PD-L2 to human PD-1 were observed (data not shown). Earlier studies showed that the CC' loop underwent a substantial conformational change when human PD-1 binds PD-L1 (17, 33). This CC' loop conformational change was even larger in the human PD-1/PD-L2 structure described in the present disclosure. Strikingly, in the absence of ligands, the CC' loop conformations of the PD-1 triple and double mutants resembled that of the ligand-bound conformations. For example, a 4.8 Å shift was observed between the $C_\alpha$ of T76 and P76 in the PD-1 triple mutant of apo-PD-1. When the triple-mutant PD-1 bound PD-L2, the sidechain of P76 maintained the same conformation. An increased population of the ligand-bound conformations in the mutant apo-PD-1 proteins was consistent with increased association constants ($k_{on}$) of the PD-1 variants.

In contrast, the conformations of the FG loop were the same in all three apo-PD-1 structures (one with an A132L substitution in the FG loop (23) and the triple and double mutants described in the present disclosure. Upon binding PD-L1 (17), there were no significant conformational changes in the FG loop. There was, however, a substantial shift in the FG loop conformation upon binding PD-L2.

Example 8: Structural Plasticity of the Human PD-1 Ligand-Binding Interface

To further investigate how the loop changes were associated with pocket formation, the apo and PD-L2-bound structures of the human triple-mutant PD-1 were superimposed (data not shown). Upon binding PD-L2, a large conformational change I in the PD-1 ligand-binding interface. A three-residue shortening of βC was observed, and βC and βF moved apart to create a deep cleft. The rearrangements that I in the pocket propagated to the edge of the FG loop, resulting in a remarkable 8.2 Å lateral shift. The overall change was less dramatic in murine PD-1. The closed architecture of the murine pocket did not require flipping of residues E84 and F63, as seen in human PD-1, and there was no secondary structure change of βC in murine PD-1. Taken together, the results described in the present disclosure provide a structural basis for systematic rearrangements at the human PD-1 ligand-binding interface coupling pocket formation and changes in the loops of PD-1 when it binds PD-L2.

Example 9: Coordinates and Structure Factors

The atomic coordinates and structure factors for human PD-1$^{N74G\ T76P\ A132V}$/PD-L2$^{IgV}$ complex, human apo-PD-1N$^{74G\ T76P\ A132V}$, and apo-PD-1$^{T76P\ A132V}$ is included as Tables 6-8, respectively, which are found in an Appendix.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 103182-1163588-003620US_Seq_Listing.txt, created on Feb. 10, 2020, and having a size of 7 kilobytes, which is filed concurrently with the specification. The sequence listing contained in this ASCII format-

REFERENCES CITED IN THIS DISCLOSURE

1. D. J. Byun, J. D. Wolchok, L. M. Rosenberg, M. Girotra, Cancer immunotherapy—immune checkpoint blockade and associated endocrinopathies. *Nat Rev Endocrinol* 10.1038/nrendo.2016.205 (2017).
2. H. Borghaei et al., Nivolumab versus Docetaxel in Advanced Nonsquamous Non-Small-Cell Lung Cancer. *N Engl J Med* 373, 1627-1639 (2015).
3. C. Robert et al., Pembrolizumab versus Ipilimumab in Advanced Melanoma. *N Engl J Med* 372, 2521-2532 (2015).
4. L. Marcus, S. J. Lemery, P. Keegan, R. Pazdur, FDA Approval Summary: Pembrolizumab for the Treatment of Microsatellite Instability-High Solid Tumors. *Clin. Cancer. Res.* 25, 3753-3758 (2019).
5. D. T. Le et al., Mismatch repair deficiency predicts response of solid tumors to PD-1 blockade. *Science* 357, 409-413 (2017).
6. A. I. Minchinton, I. F. Tannock, Drug penetration in solid tumours. *Nat. Rev. Cancer* 6, 583-592 (2006).
7. E. A. Neuwelt et al., Engaging neuroscience to advance translational research in brain barrier biology. *Nat. Rev. Neurosci.* 12, 169-182 (2011).
8. J. L. Mikitsh, A. M. Chacko, Pathways for small molecule delivery to the central nervous system across the blood-brain barrier. *Perspect Medicin Chem* 6, 11-24 (2014).
9. A. Shimabukuro-Vornhagen et al., Cytokine release syndrome. *J Immunother Cancer* 6, 56 (2018).
10. A. Sindel et al., Hematopoietic stem cell mobilization following PD-1 blockade: Cytokine release syndrome after transplantation managed with ascorbic acid. *Eur J Haematol* 103, 134-136 (2019).
11. R. J. Keizer, A. D. Huitema, J. H. Schellens, J. H. Beijnen, Clinical pharmacokinetics of therapeutic monoclonal antibodies. *Clin Pharmacokinet* 49, 493-507 (2010).
12. G. R. Jang, R. Z. Harris, D. T. Lau, Pharmacokinetics and its role in small molecule drug discovery research. *Med Res Rev* 21, 382-396 (2001).
13. J. K. Liu, The history of monoclonal antibody development—Progress, remaining challenges and future innovations. *Ann Med Surg (Lond)* 3, 113-116 (2014).
14. K. Guzik et al., Small-Molecule Inhibitors of the Programmed Cell Death-1/Programmed Death-Ligand 1 (PD-1/PD-L) Interaction via Transiently Induced Protein States and Dimerization of PD-L1. *J. Med. Chem.* 60, 5857-5867 (2017).
15. P. Jiao et al., Small molecules as PD-1/PD-L1 pathway modulators for cancer immunotherapy. *Curr. Pharm. Des.* 10.2174/1381612824666181112114958 (2018).
16. X. Cheng et al., Structure and interactions of the human programmed cell death 1 receptor. *The Journal of biological chemistry* 288, 11771-11785 (2013).
17. K. M. Zak et al., Structure of the Complex of Human Programmed Death 1, PD-1, and Its Ligand PD-L1. *Structure* 23, 2341-2348 (2015).
18. D. Y. Lin et al., The PD-1/PD-L1 complex resembles the antigen-binding Fv domains of antibodies and T cell receptors. *Proceedings of the National Academy of Sciences of the United States of America* 105, 3011-3016 (2008).
19. E. Lazar-Molnar et al., Crystal structure of the complex between programmed death-1 (PD-1) and its ligand PD-L2. *Proceedings of the National Academy of Sciences of the United States of America* 105, 10483-10488 (2008).
20. A. J. Souers et al., ABT-199, a potent and selective BCL-2 inhibitor, achieves antitumor activity while sparing platelets. *Nat. Med.* 19, 202-208 (2013).
21. C. Tovar et al., MDM2 small-molecule antagonist RG7112 activates p53 signaling and regresses human tumors in preclinical cancer models. *Cancer Res.* 73, 2587-2597 (2013).
22. X. Zhang et al., Structural and functional analysis of the costimulatory receptor programmed death-1. *Immunity* 20, 337-347 (2004).
23. E. Lazar-Molnar et al., Structure-guided development of a high-affinity human Programmed Cell Death-1: Implications for tumor immunotherapy. *EBioMedicine* 17, 30-44 (2017).
24. J. D. Bloom, An experimentally determined evolutionary model dramatically improves phylogenetic fit. *Mol. Biol. Evol.* 31, 1956-1978 (2014).
25. G. Chao et al., Isolating and engineering human antibodies using yeast surface display. *Nat Protoc* 1, 755-768 (2006).
26. J. Lyu et al., Ultra-large library docking for discovering new chemotypes. *Nature* 566, 224-229 (2019).
27. D. M. Fowler, S. Fields, Deep mutational scanning: a new style of protein science. *Nat. Methods* 11, 801-807 (2014).
28. R. L. Maute et al., Engineering high-affinity PD-1 variants for optimized immunotherapy and immuno-PET imaging. *Proceedings of the National Academy of Sciences of the United States of America* 112, E6506-6514 (2015).
29. Y. Li et al., High-affinity PD-1 molecules deliver improved interaction with PD-L1 and PD-L2. *Cancer Sci.* 109, 2435-2445 (2018).
30. J. Y. Lee et al., Structural basis of checkpoint blockade by monoclonal antibodies in cancer immunotherapy. *Nat Commun* 7, 13354 (2016).
31. S. Horita et al., High-resolution crystal structure of the therapeutic antibody pembrolizumab bound to the human PD-1. *Sci Rep* 6, 35297 (2016).
32. Z. Na et al., Structural basis for blocking PD-1-mediated immune suppression by therapeutic antibody pembrolizumab. *Cell Res.* 27, 147-150 (2017).
33. R. Pascolutti et al., Structure and Dynamics of PD-L1 and an Ultra-High-Affinity PD-1 Receptor Mutant. *Structure* 24, 1719-1728 (2016).
34. J. Yu, Y. Zhou, I. Tanaka, M. Yao, Roll: a new algorithm for the detection of protein pockets and cavities with a rolling probe sphere. *Bioinformatics* 26, 46-52 (2010).
35. M. R. Arkin, Y. Tang, J. A. Wells, Small-molecule inhibitors of protein-protein interactions: progressing toward the reality. *Chem. Biol.* 21, 1102-1114 (2014).
36. C. Corbi-Verge, P. M. Kim, Motif mediated protein-protein interactions as drug targets. *Cell Commun Signal* 14, 8 (2016).
37. A. E. Modell, S. L. Blosser, P. S. Arora, Systematic Targeting of Protein-Protein Interactions. *Trends Pharmacol. Sci.* 37, 702-713 (2016).
38. I. H. Moal, P. A. Bates, Kinetic rate constant prediction supports the conformational selection mechanism of protein binding. *PLoS Comput Biol* 8, e1002351 (2012).
39. K. G. Daniels, Y. Suo, T. G. Oas, Conformational kinetics reveals affinities of protein conformational states. *Proceedings of the National Academy of Sciences of the United States of America* 112, 9352-9357 (2015).

40. M. J. Caulfield et al., Small molecule mimetics of an HIV-1 gp41 fusion intermediate as vaccine leads. *The Journal of biological chemistry* 285, 40604-40611 (2010).
41. S. Eyrisch, V. Helms, Transient pockets on protein surfaces involved in protein-protein interaction. *J. Med. Chem.* 50, 3457-3464 (2007).
42. W. Minor, M. Cymborowski, Z. Otwinowski, M. Chruszcz, HKL-3000: the integration of data reduction and structure solution—from diffraction images to an initial model in minutes. *Acta crystallographica. Section D, Biological crystallography* 62, 859-866 (2006).
43. P. D. Adams et al., PHENIX: a comprehensive Python-based system for macromolecular structure solution. *Acta Crystallogr., Sect. D: Biol. Crystallogr.* 66, 213-221 (2010).
44. G. E. Palade, Studies on the endoplasmic reticulum. II. Simple dispositions in cells in situ. *J Biophys Biochem Cytol* 1, 567-582 (1955).
45. E. T. Boder, K. D. Wittrup, Yeast surface display for screening combinatorial polypeptide libraries. *Nat. Biotechnol.* 15, 553-557 (1997).
46. J. Lyu et al., Ultra-large library docking for discovering new chemotypes. *Nature* 566, 224-229 (2019)
47. A. Stank et al., Protein Binding Pocket Dynamics. *Acc. Chem. Res.* 49, 809-815 (2016)
48. P. Wipf et al. in *The Practice of Medicinal Chemistry* (Fourth Edition), Chapter 11, C. Wermuth et al., Eds, Academic Press, 4$^{th}$ edition, pages 279-299 (2015)
49. R. Abagyan and M. Totrov, High-throughput docking for lead generation, *Current Opinion in Chemical Biology*, Vol. 5, 375-382 (2001).
50. M. L. Lamb et al., Design, docking, and evaluation of multiple libraries against multiple targets, *Proteins*, Vol. 42, 296-318 (2001).
51. B. Waszkowycz et al. Large-scale virtual screening for discovering leads in the postgenomic era, IBM Systems Journal, Vol. 40, No. 2 (2001).
52. B. K. Shoichet et al. Molecular docking using shape descriptors, *J Comp Chem*, Vol. 13 No. 3, 380-397 (1992).
53. T. J. A. Ewing et al. Critical Evaluation of Search Algorithms for Automated Molecular Docking and Database Screening, *J. Computational Chemistry*, Vol. 18 No. 9, 1175-1189 (1997).
54. Kastenholz, M. A. et al. GRID/CPCA: A new computational tool to design selective ligands, *J. Medicinal Chemistry*, Vol. 43, 3033-3044 (2000).
55. Miller, M. D. et al. FLOG: a system to select 'quasi-flexible' ligands complementary to a receptor of known three-dimensional structure, *J. Computer-Aided Molecular Design*, Vol. 8 No. 2, 153-174 (1994).
56. Sobolev, V. et al. Molecular docking using surface complementarity, Proteins, Vol. 25, 120-129 (1996).57. Aloy, P. et al. Modeling Protein Docking using Shape Complementarity, Electrostatics and Biochemical Information, *Proteins: Structure, Function, and Genetics*, Vol. 33, 535-549 (1998).
58. Ritchie, D. W. and Kemp. G. J. L., Fast Computation, Rotation, and Comparison of Low Resolution Spherical Harmonic Molecular Surfaces, *Proteins: Structure, Function, and Genetics*, Vol. 39, 178-194 (2000).
59. Fischer, D. et al. Surface motifs by a computer vision technique: searches, detection, and implications for protein-ligand recognition, *Proteins*, Vol. 16, 278-292 (1993).
60. Rarey, M. et al. Placement of medium-sized molecular fragments into active sites of proteins, *J. Computer-Aided Molecular Design*, Vol. 10, 41-54 (1996).
61. Kramer, B. et al. Evaluation of the FlexX incremental construction algorithm for protein-ligand docking, *Proteins*, Vol. 37, 228-241 (1999).
62. Rarey, M. et al. A Fast Flexible Docking Method Using An Incremental Construction Algorithm, *J. Mol. Biol.*, Vol. 261, 470-489 (1996).
63. Welch, W. et al. Hammerhead: Fast, fully automated docking of flexible ligands to protein binding sites, *Chemical Biology*, Vol. 3, 449-462 (1996).
64. Leach, A. R., Kuntz, I.D., Conformational Analysis of Flexible Ligands in Macromolecular Receptor Sites, *J. Comp. Chem., Vol.* 13, 730-748 (1992).
65. Bohm, H. J., The computer program LUDI: a new method for the de novo design of enzyme inhibitors, *J. Computer-Aided Molecular Design*, Vol. 6, 61-78 (1992).
66. Bohacek, R. S. and McMartin, C., Multiple Highly Diverse Structures Complementary to Enzyme Binding Sites: Results of Extensive Application of a de Novo Design Method Incorporating Combinatorial Growth, *J. American Chemical Society*, Vol. 116, 5560-5571 (1994).
67. DesJarlais, R. L. et al. Docking Flexible Ligands to Macromolecular Receptors by Molecular Shape, *J. Med. Chem.*, Vol. 29, 2149-2153 (1986).
68. Claussen, H. et al. FlexE: Efficient Molecular Docking Considering Protein Structure Variations, *J. Molecular Biology*, Vol. 308, 377-395 (2001).
69. Abagyan, R. A. et al. Biased probability Monte Carlo conformational searches and electrostatic calculations for peptides and proteins, *J. Comp. Chem.*, Vol. 15, 488-506 (1994).
70. Halgren, T. A. et al. Glide: a new approach for rapid, accurate docking and scoring. 2. Enrichment factors in database screening, *J Med Chem.*, Vol. 47 No. 7, 1750-1759, (2004).
71. Luty, B. A. et al. Molecular Mechanics/Grid Method for the Evaluation of Ligand-Receptor Interactions, *J. Comp. Chem.*, Vol. 16, 454-464 (1995).
72. Goodsell et al. Automated Docking of Substrates to Proteins by Simulated Annealing, *Proteins: Structure, Function, and Genetics*, Vol. 8, 195-202 (1990).
73. Jones, G. et al. Molecular Recognition of Receptor Sites using a Genetic Algorithm with a Description of Desolvation, *J. Mol. Biol.*, Vol. 245, 43-53 (1995).
74. Jones, G. et al. Development and Validation of a Genetic Algorithm for Flexible Docking, *J. Mol. Biol., Vol.* 267, 727-748 (1997).
75. Taylor, J. S. and Burnett, R. M., *Proteins*, Vol. 41, 173-191 (2000).
76. Morris, G. M. et al. Automated Docking Using a Lamarckian Genetic Algorithm and an Empirical Binding Free Energy Function, *J. Comp. Chem.*, Vol. 19, 1639-1662 (1998).
77. Di Nola, A. et al. Molecular Dynamics Simulation of the Docking of Substrates to Proteins, *Proteins*, Vol. 19, 174-182 (1994).
78. Wang, J. et al. *Proteins*, Vol. 36, 1-19 (1999).79. Bohm, H. J., The Development of a simple empirical scoring function to estimate the binding constant for a protein-ligand complex of known three-dimensional structure, *J. Comput-Aided Mol. Des.*, Vol. 8, 243-256 (1994).
80. Wang, R. et al. A new empirical method for estimating the binding affinity of a protein-ligand complex., *J. Molecular Modeling*, Vol. 4, 379 (1998).
81. Eldridge, M. D. et al. Empirical scoring functions: I. The development of a fast empirical scoring function to esti- 81. mate the binding affinity of ligands in receptor complexes, *J. Computer-Aided Molecular Design*, Vol. 11, 425-445 (1997).
82. Gelhaar, D. K. et al. In *Rational Drug Design: Novel Methodology and Practical Applications*, Parrill, L., Reddy, M. R., Ed.; American Chemical Society: Washington, D.C., pp. 292-311(1999).
83. Rognan D. et al. *J. Medicinal Chemistry*, Vol. 42, 4650-4658 (1999).
84. Halgren, T. A. et al. Glide: a new approach for rapid, accurate docking and scoring. 2. Enrichment factors in database screening, *J Med Chem.*, Vol. 47 No. 7, 1750-1759 (2004).
85. Pearlman, D. A. et al. *AMBER* 4.1, University of California, San Francisco (1995).
86. Cornell, W. D. et al. A second-generation force field for the simulation of proteins, nucleic acids, and organic molecules, *J. American Chemical Society*, Vol. 117, 5179-5197 (1995).
87. Jorgensen, W. L., & Tirado-Rives, J., *J. American Chemical Society*, Vol. 110, 1657-1666 (1988).
88. Halgren, T. A., Merck Molecular Force Field. I. Basis, Form, Scope, Parameterization, and Performance of MMFF94, *J. Comp. Chem.*, Vol. 17, 490-519 (1996).
89. Brooks, B. R. et al. CHARMM: A Program for Macromolecular Energy, Minimization, and Dynamics Calculations, J. Comp. Chem., Vol. 4, 187-217 (1983).
90. Stewart, J. J. P., *Quantum Chemistry Program Exchange*, Vol. 10:86 (1990).
91. Liotard, D. A. et al. *Quantum Chemistry Program Exchange*—no. 506, QCPE Bulletin, Vol. 9: 123 (1989).
92. AMSOL-version 6.5.1 by G. D. Hawkins et al. University of Minnesota, Minneapolis (1997).
93. Gohlke, H. et al. Knowledge-based Scoring Function to Predict Protein-Ligand Interactions, *J. Mol. Biol.*, Vol. 295, 337-356 (2000).
94. Muegge, I. and Martin, Y. C., A general and fast scoring function for protein-ligand interactions—a simplified potential approach., *J. Med. Chem.*, Vol. 42, 791-804 (1999).
95. Mitchell, J. B. O. et al. BLEEP—Potential of Mean Force Describing Protein-Ligand Interactions II. Calculation of Binding Energies and Comparison with Experimental Data, *J. Comp. Chem.*, Vol. 20, 1165-1176 (1999).
96. Head, R. D. et al. VALIDATE: A New Method for Receptor-Based Prediction of Binding Affinities of Novel Ligand, *J. American Chemical Society*, Vol. 118, 3959-3969 (1996).
97. Bissantz, C. et al. Protein-based virtual screening of chemical databases. 1. Evaluation of different docking/scoring combinations, *J Med Chem*, Vol. 43, 4759-4767 (2000).
98. Gilson, M. K., and Honig, B., Calculation of the Total Electrostatic Energy of a Macromolecular System: Solvation Energies, Binding Energies, and Conformational Analysis, *Proteins*, Vol. 4, 7-18 (1988).
99. Mehler, E. L. and Solmajer, T., Electrostatic effects in proteins: comparison of dielectric and charge models *Protein Engineering*, Vol. 4, 903-910 (1991).
99. Hoist, M. et al. Adaptive Multilevel Finite Element Solution of the Poisson-Boltzmann Equations I. Algorithms and Examples, *J. Comp. Chem.*, Vol. 21, No. 15, 1319-1342 (2000).
100. Nicholls, A., and Honig, B., A Rapid Finite Difference Algorithm, Utilizing Successive Over-Relaxation to Solve Poisson-Boltzmann Equation, *J. Comp. Chem.*, Vol. 12, No. 4, 435-445 (1991)
101. Still, W. C. et al. A General Treatment of Solvation for Molecular Mechanics, *J. Am. Chem. Soc.*, Vol. 112, 6127-6129 (1990).
102. Ghosh, A. et al. A Generalized Born Model Based on Surface Integral Formulation, *J. Physical Chemistry B.*, Vol. 102, 10983-10 (1988).
103. Eisenberg, D., and McLachlan, A. D., Solvation Energy in Protein Folding and Binding, *Nature*, Vol. 31, 3086 (1986).
104. Privalov, P. L., and Makhatadze, G. I., Contribution of hydration to protein folding thermodynamics, *J. Mol. Bio.*, Vol. 232, 660-679 (1993).
105. Stouten, P. F. W. et al. An effective solvation term based on atomic occupancies for use in protein simulations, *Molecular Simulation*, Vol. 10, No. 2-6, 97-120 (1993).
106. Bash, P. et al. Free Energy Calculation by Computer Simulation, *Science*, Vol. 236, 564 (1987).
107. Jorgensen, W. L. et al. Relative Partition Coefficients for Organic Solutes from Fluid Simulations, *J. Phys. Chem.*, Vol. 94, 1683-1686 (1990).
108. Jackson, R. M. Rapid Refinement of Protein Interfaces Incorporating Solvation: Application to the Docking Problem, *J. Mol. Biol.*, Vol. 276, 265-285 (1998).
109. Labanowski and J. Andzelm, editors, Density Functional Methods in Chemistry, Springer-Verlag, New York (1991).
110. LaBute et al. Adverse Drug Reaction Prediction Using Scores Produced by Large-Scale Drug-Protein Target Docking on High-Performance Computing Machines, *PloS One* 9(9): e106298 (2014)
111. Wang et al. TargetHunter: An In Silico Target Identification Tool for Predicting Therapeutic Potential of Small Organic Molecules Based on Chemogenic Database, *The AAPS Journal* 15(2): 395-406 (2013)
112. Keiser, M. J. (2015) In Silico Prediction of Drug Side Effects, in Antitargets and Drug Safety (eds L. Urbán, V. F. Patel and R. J. Vaz), Wiley-VCH Verlag GmbH & Co. KGaA, Weinheim, Germany.
113. Bowes et al. Reducing safety-related drug attrition: The use of in vitro pharmacological profiling, *Nature Review Drug Discovery* 11:909 (2012)
114. Erlanson D. A. (2011) Introduction to Fragment-Based Drug Discovery. In: Davies T., Hyvönen M. (eds) Fragment-Based Drug Discovery and X-Ray Crystallography. *Topics in Current Chemistry*, vol 317. Springer, Berlin, Heidelberg 115. Murray, C., Rees, D. The rise of fragment-based drug discovery. *Nature Chem.* 1:187-192 (2009)
116. Jutz et al. A cellular platform for the evaluation of immune checkpoint molecules. Oncotarget 8(39):64892-64906 (2017)
117. Ganesan, A. et al. Comprehensive in vitro characterization of PD-L1 small molecule inhibitors. *Sci Rep* 9:12392 (2019)
118. Selby et al. Preclinical Development of Ipilimumab and Nivolumab Combination Immunotherapy: Mouse Tumor Models, In Vitro Functional Studies, and Cynomolgus Macaque Toxicology. *PLoS One September* 9; 11(9): e0161779 (2016)

In the foregoing description, numerous specific details are set forth to provide a more thorough understanding of the present invention. However, it will be apparent to one of skill in the art that the invention described in this disclosure may be practiced without one or more of these specific details. In other instances, well-known features and procedures well known to those skilled in the art have not been described in order to avoid obscuring the invention. Embodiments of the disclosure have been described for illustrative and not restrictive purposes. Although the present invention is described primarily with reference to specific embodiments, it is also envisioned that other embodiments will become apparent to those skilled in the art upon reading the present disclosure, and it is intended that such embodiments be contained within the present inventive methods. Accordingly, the present disclosure is not limited to the embodiments described above or depicted in the drawings, and various embodiments and modifications can be made without departing from the scope of the claims below. All publications, patents, and patent applications cited herein are hereby incorporated by reference in their entirety for all purposes.

The invention claimed is:

1. A method for identifying a small molecule capable of binding to a PD-L2 binding pocket of human PD-1, the method comprising:
   I) screening in silico a small molecule library for candidate small molecules capable of binding to the PD-L2 binding pocket of human PD-1, wherein a three-dimensional model of the PD-L2 binding pocket of human PD-1 is computationally derived from atomic coordinates corresponding to crystals of a variant of human PD-1 comprising amino acid substitutions in each of residues corresponding to N74, T76 or A132 of SEQ ID NO: 1; and,
   II) evaluating the candidate small molecules identified in step (I) through one or more in vitro or in vivo assays for their ability to bind to the PD-L2 binding pocket of human PD-1 to thereby identify the small molecule capable of binding to the PD-L2 binding pocket of human PD-1.

2. The method of claim 1, wherein the atomic coordinates are listed in Table 6.

3. The method of claim 1, wherein in step (I) the small molecule library is screened using computational docking for the candidate small molecules, and wherein the screening of the small molecule library to identify a candidate small molecule includes:
   determining a docking score between the candidate small molecule and the PD-L2 binding pocket of human PD-1;
   comparing the docking score to a threshold for binding to the PD-L2 binding pocket of human PD-1; and,
   identifying the candidate small molecule based on the docking score being above the threshold.

4. The method of claim 3, wherein the docking score takes into account one or more interactions of (a) to (k):
   a) the candidate small molecules interact via hydrogen bonds with one or more amino acid residues in the PD-L2 binding pocket of human PD-1;
   b) the candidate small molecules interact via hydrogen bonds with the PD-L2 binding pocket of human PD-1;
   c) the candidate small molecules interact via ionic interactions with one or more amino acid residues in the PD-L2 binding pocket of human PD-1;
   d) the candidate small molecules interact via ionic interactions with the PD-L2 binding pocket of human PD-1;
   e) the candidate small molecules interact via one or more water molecules with one or more amino acid residues in the PD-L2 binding pocket of human PD-1;
   f) the candidate small molecules interact via one or more water molecules with the PD-L2 binding pocket of human PD-1;
   g) the candidate small molecules interact via π-π interactions with one or more amino acid residues in the in the PD-L2 binding pocket of human PD-1;
   h) the candidate small molecules interact via van der Waals interactions to one or more amino acid residues in the in the PD-L2 binding pocket of human PD-1;
   i) the candidate small molecules interact via van der Waals interactions with the PD-L2 binding pocket of human PD-1;
   j) the candidate small molecules interact via steric interactions to one or more amino acid residues in the in the PD-L2 binding pocket of human PD-1;
   k) the candidate small molecules interact via steric interactions with the PD-L2 binding pocket of human PD-1.

5. The method of claim 3, wherein the computational docking comprises computationally docking three-dimensional structures of small molecules from the small molecule library onto surface exposed amino acid residues of the three-dimensional model of the PD-L2 binding pocket of human PD-1.

6. The method of claim 5, wherein the surface exposed amino acid residues comprise one or more amino acids corresponding to F63, V64, N66, Y68, E84, L122, I126, I134 or E136 of SEQ ID NO:1.

7. The method of claim 5, wherein the computational docking comprises sampling and scoring a plurality of docked orientations of the small molecules relative to the three-dimensional model of the PD-L2 binding pocket of human PD-1.

8. The method of claim 7, wherein the scoring comprises determining, for complexes of the small molecules and the PD-L2 binding pocket of human PD-1, one or more of binding forces, configurational entropy, local minima in a Gibbs free energy landscape, or energy barriers between the local minima in the Gibbs free energy landscape, or combinations of two or more thereof.

9. The method of claim 5, wherein the computational docking further comprises assigning a distance cutoff to match atoms of the small molecules to surface exposed atoms of the PD-L2 binding pocket of human PD-1.

10. The method of claim 9, wherein the surface exposed atoms comprise one or more of CB of F63, CE1 of F63, CD1 of F63, CE1 of F63, CG2 of V64, CG2 of V64, O of V64, ND2 of N66, ND2 of N66, CE1 of Y68, OH of Y68, OE1 of E84, OE2 of E84, OE2 of E84, OE1 of E84, OE2 of E84, OE1 of E84, CD1 of L122, CG2 of I126, CD1 of I126, CD1 of I126, CG2 of I126, CD1 of I126, CB of I134, CG1 of I134, CG1 of I134, CD1 of I134, CD1 of I134, OE2 of E136, OE2 of E136 or OE2 of E136, wherein numbering of amino acids containing the surface exposed atoms is based on SEQ ID NO: 1.

11. The method of claim 1, wherein step (I) comprises performing one or more of molecular dynamic simulations, kinetic Monte Carlo (KMC) simulations, direct simulations Monte Carlo (DSMC), or density functional theory (DFT) simulations to determine if a small molecule binds to the PD-L2 binding pocket of human PD-1, thereby identifying the candidate small molecules that bind to the PD-L2 binding pocket of human PD-1.

12. The method of claim 1, further comprising testing the small molecule capable of binding to the PD-L2 binding pocket of human PD-1 in an in vitro or in vivo assay to determine its anti-cancer efficacy.

13. The method of claim 12, further comprising determining by an in vitro or in vivo assay if the small molecule capable of binding to the PD-L2 binding pocket of human PD-1 has an off-target effect.

14. The method of claim 1, further comprising testing toxicity of the small molecule capable of binding to the PD-L2 binding pocket of human PD-1 by an in vitro or in vivo toxicity assay.

15. A method for identifying a ligand capable of binding to a PD-L2 binding pocket of human PD-1, the method comprising:
I) identifying in silico a test ligand capable of interacting with the PD-L2 binding pocket of human PD-1, wherein a three-dimensional model of the PD-L2 binding pocket of human PD-1 is computationally derived from atomic coordinates corresponding to crystals of a variant of human PD-1 comprising amino acid substitutions in each of residues corresponding to N74, T76 or A132 of SEQ ID NO:1; and,
II) evaluating the test ligand identified in step (I) through one or more in vitro or in vivo assays for its ability to bind to the PD-L2 binding pocket of human PD-1 to thereby identify the ligand capable of binding to the PD-L2 binding pocket of human PD-1.

16. The method of claim 15, wherein the atomic coordinates are listed in Table 6.

17. The method of claim 15, wherein in step (I) the test ligand is identified using computational docking, comprising:
determining a docking score between a candidate ligand and the PD-L2 binding pocket of human PD-1;
comparing the docking score to a threshold for binding to the PD-L2 binding pocket of human PD-1; and,
identifying the test ligand based on the docking score being above the threshold.

18. The method of claim 17, wherein the docking score takes into account one or more interactions of (a) to (k):
a) the candidate ligand interacts via hydrogen bonds with one or more amino acid residues in the PD-L2 binding pocket of human PD-1;
b) the candidate ligand interacts via hydrogen bonds with the PD-L2 binding pocket of human PD-1;
c) the candidate ligand interacts via ionic interactions with one or more amino acid residues in the PD-L2 binding pocket of human PD-1;
d) the candidate ligand interacts via ionic interactions with the PD-L2 binding pocket of human PD-1;
e) the candidate ligand interacts via one or more water molecules with one or more amino acid residues in the PD-L2 binding pocket of human PD-1;
f) the candidate ligand interacts via one or more water molecules with the PD-L2 binding pocket of human PD-1;
g) the candidate ligand interacts via $\pi$-$\pi$ interactions with one or more amino acid residues in the in the PD-L2 binding pocket of human PD-1;
h) the candidate ligand interacts via van der Waals interactions to one or more amino acid residues in the in the PD-L2 binding pocket of human PD-1;
i) the candidate ligand interacts via van der Waals interactions with the PD-L2 binding pocket of human PD-1;
j) the candidate ligand interacts via steric interactions to one or more amino acid residues in the in the PD-L2 binding pocket of human PD-1;
k) the candidate ligand interacts via steric interactions with the PD-L2 binding pocket of human PD-1.

19. The method of claim 17, wherein the computational docking comprises computationally docking a three-dimensional structure of the candidate ligand onto surface exposed amino acid residues of the three-dimensional model of the PD-L2 binding pocket of human PD-1.

20. The method of claim 19, wherein the surface exposed amino acid residues comprise one or more amino acids corresponding to F63, V64, N66, Y68, E84, L122, I126, I134 or E136 of SEQ ID NO:1.

21. The method of claim 19, wherein the computational docking comprises sampling and scoring a plurality of docked orientations of the candidate ligand relative to the three-dimensional model of the PD-L2 binding pocket of human PD-1.

22. The method of claim 21, wherein the scoring comprises determining, for complexes of the candidate ligand and the PD-L2 binding pocket of human PD-1, one or more of binding forces, configurational entropy, local minima in a Gibbs free energy landscape, or energy barriers between the local minima in the Gibbs free energy landscape, or combinations of two or more thereof.

23. The method of claim 19, wherein the computational docking further comprises assigning a distance cutoff to match atoms of the candidate ligand to surface exposed atoms of the PD-L2 binding pocket of human PD-1.

24. The method of claim 23, wherein the surface exposed atoms comprise one or more of CB of F63, CE1 of F63, CD1 of F63, CE1 of F63, CG2 of V64, CG2 of V64, O of V64, ND2 of N66, ND2 of N66, CE1 of Y68, OH of Y68, OE1 of E84, OE2 of E84, OE2 of E84, OE1 of E84, OE2 of E84, OE1 of E84, CD1 of L122, CG2 of I126, CD1 of I126, CD1 of I126, CG2 of I126, CD1 of I126, CB of I134, CG1 of I134, CG1 of I134, CD1 of I134, CD1 of I134, OE2 of E136, OE2 of E136 or OE2 of E136, wherein numbering of amino acids containing the surface exposed atoms is based on SEQ ID NO: 1.

25. The method of claim 15, wherein step (I) comprises performing one or more of molecular dynamic simulations, kinetic Monte Carlo (KMC) simulations, direct simulations Monte Carlo (DSMC), or density functional theory (DFT) simulations to determine the test ligand that binds to the PD-L2 binding pocket of human PD-1.

26. The method of claim 15, further comprising testing the ligand capable of binding to the PD-L2 binding pocket of human PD-1 in an in vitro or in vivo assay to determine its anti-cancer efficacy.

27. The method of claim 26, further comprising determining by an in vitro or in vivo assay if the ligand capable of binding to the PD-L2 binding pocket of human PD-1 has an off-target effect.

28. The method of claim 15, further comprising testing toxicity of the ligand capable of binding to the PD-L2 binding pocket of human PD-1 by an in vitro or in vivo toxicity assay.

29. The method of claim 15, wherein the test ligand is a small molecule.

\* \* \* \* \*

UNITED STATES PATENT AND TRADEMARK OFFICE
CERTIFICATE OF CORRECTION

| | |
|---|---|
| PATENT NO. | : 10,684,287 B1 |
| APPLICATION NO. | : 16/786409 |
| DATED | : June 16, 2020 |
| INVENTOR(S) | : Shaogeng Tang and Peter S. Kim |

It is certified that error appears in the above-identified patent and that said Letters Patent is hereby corrected as shown below:

In the Claims

In Column 53, Line 34:
In Claim 1, delete "NO: 1;" and insert -- NO:1; --.

In Column 54, Line 29-30:
In Claim 4, delete "in the in the" and insert -- in the --.

In Column 54, Line 33:
In Claim 4, delete "in the in the" and insert -- in the --.

In Column 54, Line 38:
In Claim 4, delete "in the in the" and insert -- in the --.

In Column 56, Line 14 (Approx.):
In Claim 18, delete "in the in the" and insert -- in the --.

In Column 56, Line 17 (Approx.):
In Claim 18, delete "in the in the" and insert -- in the --.

In Column 56, Line 22:
In Claim 18, delete "in the in the" and insert -- in the --.

In Column 55, Line 2-3:
In Claim 10, delete "CD1 of F63, CE1 of F63, CG2 of V64, CG2 of V64," and insert -- CD1 of F63, CG2 of V64, --.

In Column 55, Line 4:
In Claim 10, delete "ND2 of N66, ND2 of N66," and insert -- ND2 of N66, --.

Signed and Sealed this
Twenty-ninth Day of August, 2023

*Katherine Kelly Vidal*

Katherine Kelly Vidal
*Director of the United States Patent and Trademark Office*

CERTIFICATE OF CORRECTION (continued)
U.S. Pat. No. 10,684,287 B1

In Column 55, Line 5-7:
In Claim 10, delete "OE2 of E84, OE2 of E84, OE1 of E84, OE2 of E84, OE1 of E84, CD1 of L122, CG2 of I126, CD1 of I126, CD1 of I126, CG2 of I126, CD1 of I126" and insert -- OE2 of E84, CD1 of L122, CG2 of I126 --.

In Column 55, Line 7-9:
In Claim 10, delete "CG1 of I134, CG1 of I134, CD1 of I134, CD1 of I134, OE2 of E136, OE2 of E136 or OE2 of E136," and insert -- CG1 of I134, CD1 of I134, or OE2 of E136 --.

In Column 56, Line 53:
In Claim 24, delete "CD1 of F63, CE1 of F63, CG2 of V64, CG2 of V64," and insert -- CD1 of F63, CG2 of V64, --.

In Column 56, Line 54:
In Claim 24, delete "ND2 of N66, ND2 of N66," and insert -- ND2 of N66, --.

In Column 56, Line 55-56:
In Claim 24, delete "OE2 of E84, OE2 of E84, OE1 of E84, OE2 of E84, OE1 of E84," and insert -- OE2 of E84, --.

In Column 56, Line 56-59:
In Claim 24, delete "CD1 of I126, CD1 of I126, CG2 of I126, CD1 of I126, CB of I134, CG1 of I134, CG1 of I134, CD1 of I134, CD1 of I134, OE2 of E136, OE2 of E136 or OE2 of E136," and insert -- CB of I134, CG1 of I134, CD1 of I134, or OE2 of E136, --.